United States Patent
Hanna et al.

[11] Patent Number: 6,063,138
[45] Date of Patent: May 16, 2000

[54] METHOD AND APPARATUS FOR THE FORMATION OF PARTICLES

[75] Inventors: Mazen Hanna, Bradford; Peter York, Ilkley, both of United Kingdom

[73] Assignee: Bradford Particle Design Limited, Bradford, United Kingdom

[21] Appl. No.: 08/765,540

[22] PCT Filed: Jun. 30, 1995

[86] PCT No.: PCT/GB95/01523

§ 371 Date: Feb. 19, 1997

§ 102(e) Date: Feb. 19, 1997

[87] PCT Pub. No.: WO96/00610

PCT Pub. Date: Jan. 11, 1996

[30] Foreign Application Priority Data

Jun. 30, 1994 [GB] United Kingdom ................... 9413202

[51] Int. Cl.$^7$ ................................ B01J 2/04; B01D 9/02
[52] U.S. Cl. ..................... 23/295 R; 23/300; 422/245.1
[58] Field of Search ................................ 23/295 R, 300; 432/245.1

[56] References Cited

U.S. PATENT DOCUMENTS 5,043,280  8/1991  Fischer et al. ...................... 435/235.1

FOREIGN PATENT DOCUMENTS 542314    5/1993   European Pat. Off. .
11-76437  7/1989   Japan .
50-57166  8/1991   Japan .
90-03782  4/1990   WIPO .

*Primary Examiner*—Gary P. Straub
*Attorney, Agent, or Firm*—Townsend and Townsend and Crew LLP

[57] ABSTRACT

The invention provides a method for forming particles of a substance, by co-introducing into a particle formation vessel, in which the temperature and pressure are controlled, of a supercritical fluid; a solution or suspension of the substance in a first vehicle; and a second vehicle which is both substantially miscible with the first vehicle and substantially soluble in the supercritical fluid, in such a way that dispersion of the solution or suspension and the second vehicle, and extraction of the vehicles, occur substantially simultaneously and substantially immediately on introduction of the fluids into the vessel, by the action of the supercritical fluid. Preferably the solution/suspension of the substance is introduced separately from the second vehicle, in such a way that contact between the solution/suspension and the second vehicle occurs either substantially simultaneously with, or immediately before, their dispersion by the supercritical fluid and extraction of the vehicles by the supercritical fluid. The method allows a high degree of control over the size, shape, crystalline form and other physico-chemical properties of the particulate product The invention also provides apparatus for carrying out such a method, using a coaxial nozzle to introduce the fluids into the particle formation vessel, and a particulate product made using the method or the apparatus.

22 Claims, 15 Drawing Sheets

METHOD AND APPARATUS FOR THE FORMATION OF PARTICLES

BACKGROUND OF THE INVENTION

1. Field of the Invention

This invention relates to the controlled formation of particulate products using supercritical fluids. It provides a method and apparatus for the formation of a substance in particulate form, and the particulate product of such a method.

2. Description of Prior Art

The use of supercritical fluids (SCFs) and the properties thereof have been extensively documented; see for instance J. W. Tom and P. G. Debenedetti, "Particle Formation with Supercritical Fluids—A Review", *J. Aerosol. Sci.*, 22 (5), pp555–584 (1991). Briefly, a supercritical fluid can be defined as a fluid at or above its critical pressure (Pc) and critical temperature (Tc) simultaneously. Such fluids have been of considerable interest, because of their unique properties. These characteristics include:

High diffusivity, low viscosity and low surface tension compared with liquids.

High compressibility compared with the ideal gas implies large changes in fluid density with only slight changes in pressure, which in turn results in highly controllable solvation power. Supercritical fluid densities typically range from 0.1–0.9 g/ml under normal working conditions. Thus, selective extraction with one supercritical fluid is possible.

Many supercritical fluids are normally gases under ambient conditions, which eliminates the evaporation/concentration step needed in conventional liquid extractions.

Most of the commonly used supercritical fluids create non-oxidizing or non-degrading atmospheres for sensitive and thermolabile compounds, due to their inertness and the moderate temperatures used in routine working conditions. Carbon dioxide is the most extensively used SCF due to its cheapness, non-toxicity, non-flammability and low critical temperature.

These characteristics have led to the development of several techniques of extraction and particle formation utilising supercritical fluids. In particular, two particle formation methods have been identified.

"Rapid expansion of supercritical solution" (RESS) (see, for instance, J. W. Tom and P. G. Debenedetti, supra) involves the dissolution of the solute of interest in a supercritical fluid, followed by rapid expansion of the resulting supercritical solution to atmospheric pressure, resulting in the precipitation of solute particles.

"Gas anti solvent" (GAS) recrystallisation (P. M. Gallagher et al, "Supercritical Fluid Science and Technology", *ACS Symp. Ser.*, 406, p334 (1989)) is particularly useful in situations when the solute of interest does not dissolve in, or has a very low solubility in, a supercritical fluid or a modified supercritical fluid. In this technique, the solute is dissolved in a conventional solvent. A supercritical fluid such as carbon dioxide is introduced into the solution, leading to a rapid expansion of its volume. As a result, the solvent power decreases dramatically over a short period of time, triggering the precipitation of particles.

The concept of spraying liquid mixtures into supercritical fluids such as carbon dioxide, or vice versa, has also been employed in solvent extraction procedures for a decade (see for instance R. J. Lahiere & J. R. Fair in *Ind. Eng. Chem. Res.*, 26, pp2086–2092 (1987)).

More recently, U.S. Pat. No. 5,043,280 describes a method for manufacturing a preparation comprising a substance, such as a medically useful substance, and a carrier, such as a pharmaceutically acceptable carrier, which avoids or lacks a solvent residue, or at least reduces the solvent residue to a toxicologically harmless amount. The method essentially involves the use of a fluid, at a supercritical state when introduced into a spray tower, to extract a solvent from sprayed solution(s) of a substance and a carrier, to form a sterile product containing the substance embedded in the carrier. It should be noted, however, that the method has no means for controlling the physical properties of the particulate product formed.

In many fields, and especially in the fields of pharmaceuticals, photographic materials, ceramics, explosives and dyes, there is a need for techniques whereby a particulate product may be obtained with consistent and controlled physical criteria, including particle size and shape, quality of the crystalline phase, chemical purity and enhanced handling and fluidizing properties.

In addition, it would be advantageous to be able to prepare micron-sized particles directly, without the need to mill products to that size range. Such milling can lead to associated problems such as increased static charge and enhanced particle cohesiveness, as well as reduced product yield.

A further method for forming particulate products using supercritical fluids has been described more recently in our co-pending PCT patent application, no.

PCT/GB94/01426 of Jun. 30, 1994, which claims priority from UK patent application no. 9313650.5 of Jul. 1, 1993 and was published as WO-95/01221. In the method described in that patent application, a substance to be produced in particulate form is dissolved or suspended in an appropriate vehicle. The resulting solution or suspension is then co-introduced into a particle formation vessel with a supercritical fluid (preferably through a co-axial nozzle) in such a way that dispersion and extraction of the vehicle occur substantially simultaneously by the action of the supercritical fluid, and substantially immediately on introduction of the fluids into the vessel. The pressure and temperature inside the particle formation vessel are carefully controlled during this process.

This method allows a high degree of control over conditions such as pressure and temperature and fluid flow rates, at the exact point where particle formation occurs (i.e. at the point where the vehicle is extracted into the supercritical fluid). It therefore allows great control over the size and shape of the particles formed, and over other physical and/or chemical properties of the particles, including the polymorphic form where several are possible. The method is thus ideal for producing particles for use in fields where such high levels of control are necessary, for instance in the manufacture of pharmaceuticals, photographic materials, ceramics, etc. The method obviates the need for milling particulate products to a desired size range, thus eliminating the disadvantages of increased static charge, enhanced particle cohesiveness and reduced product yield, described above.

The applications of this and other particle formation techniques using supercritical fluids are, however, limited. The vehicle chosen must be soluble in the chosen supercritical fluid. Also, the substance itself, from which particles are to be formed, must be capable of dissolution, or at least suspension, in the chosen vehicle. It is not always easy to select a vehicle that can both dissolve the substance and also itself dissolve in the supercritical fluid being used (in practice, usually carbon dioxide).

An example of a situation in which such problems arise is the preparation of lactose. Lactose is commonly used as a carrier for pharmaceuticals, in tablets and capsule formulations and in particular for drugs to be delivered by inhalation methods. It thus needs to be prepared in the form of particles which have, among other characteristics, a narrow size distribution, a high purity and an appropriate particle shape.

However, lactose has very low solubility in conventional organic solvents which might be used with supercritical carbon dioxide in known particle formation techniques. Lactose dissolves readily in water, but water will not dissolve in supercritical carbon dioxide. It has thus, previously, been very difficult to form lactose particles directly from aqueous solution using known supercritical fluid techniques (including that described in WO-95/01221), since the supercritical fluid (typically carbon dioxide) would not extract water from the aqueous solution, or would do it so slowly as to be impractical. Nevertheless, it would be generally desirable to be able to form lactose particles in the controlled manner that supercritical fluid techniques (in particular that described in WO-95/01221) would allow.

It is generally known that other sugars and many amino acids and proteins suffer from similar disadvantages to that of lactose, ie. they have very low solubility in organic solvents and supercritical fluids/modified supercritical fluids (see Stahl et al, "Dense Gas Extraction on a Laboratory Scale: A Survey of some Recent Results", *Fluid Phase Equilibria*, 10, p269, 1983) and cannot therefore be formed into particles using former supercritical fluid particle formation techniques (RESS in particular). Again, as with lactose, it would be desirable to be able to produce particulate forms of such compounds in a controlled manner, for instance for use in pharmaceuticals and foodstuffs.

A related problem arises with many proteins. Although solutions of such proteins in organic solvents can be prepared, it is generally undesirable to do so because of the risk of the protein unfolding and denaturing (see, for instance, K. A. Dill & D. Shortle, *Ann. Rev. Biochem.*, 1991, 60, pp795–825, especially p813) Thus, it is difficult if not impossible, to prepare. particulate products of such proteins, with acceptable biological activity, using known supercritical fluid particle formation techniques.

There are many other examples of substances which might otherwise be formed into particles using supercritical fluids, but which cannot be sufficiently well dissolved or suspended in an appropriate solvent which will itself dissolve in a useful supercritical fluid.

There is therefore a need to solve this problem, to allow the use of supercritical fluid particle formation techniques (including the extremely effective technique described in WO-95/01221) for substances such as lactose. and proteins. The present invention sets out to overcome, or at least mitigate, the problem.

SUMMARY OF THE INVENTION

According to a first aspect of the present invention, there is provided a method for forming particles of a substance, the method comprising the co-introduction into a particle formation vessel, the temperature and pressure in which are controlled, of a supercritical fluid; a solution or suspension of the substance in a first vehicle; and a second vehicle which is both substantially miscible with the first vehicle and substantially soluble in the supercritical fluid, in such a way that dispersion of the solution or suspension and the second vehicle and extraction of the vehicles by the supercritical fluid occur substantially simultaneously and substantially immediately on introduction of the fluids into the particle formation vessel.

As will be explained below, contact between the solution or suspension and the second vehicle may occur either at much the same time as, or slightly before, dispersion and extraction, by the suoercritical fluid—the timing will depend on the nature of the substance from which particles are to be formed, and the nature of the desired end product.

In other versions of the process, useful or advantageous results may still be achieved even if the first and second vehicles meet substantially before introduction to the vessel.

The substance will typically (although not always) be one which, as described above, is soluble or substantially soluble only in solvents which are themselves substantially insoluble in the supercritical fluid. It may be a substance which, though soluble in an appropriate supercritical fluid-soluble solvent, would suffer detrimental effects if dissolved in that solvent prior to particle formation (for instance, a hydrophilic protein), or be otherwise incompatible with such a solvent. It is preferably substantially soluble, however, in the first vehicle.

As used herein, the term "supercritical fluid" means a fluid substantially at or above its critical pressure (Pc) and critical temperature (Tc) simultaneously. In practice, the pressure of the fluid is likely to be in the range (1.01–7.0)Pc, and its temperature in the range (1.01–4.0)Tc.

The term "vehicle" means a fluid which is able to carry a solid or solids in solution or suspension. Each vehicle may be composed of one or more component fluids. Both vehicles may be substantially soluble in the chosen supercritical fluid, although it is only essential that the second vehicle has this characteristic.

As used herein, the term "supercritical solution" means a supercritical fluid together with a vehicle or vehicles, as defined above, which it has extracted and dissolved. The solution should itself still be in the supercritical state.

The term "dispersion" means the formation of droplets, or other analogous fluid elements, of the solution or suspension and/or the second vehicle.

The term "substance" includes substances in a single-component or multi-component (e.g. an intimate mixture, or one component in a matrix of another) form.

The present invention relies on the dissolution or suspension of the substance of interest in a first vehicle, in which it is preferably substantially soluble, with "dilution" of the resultant solution or suspension, either beforehand or substantially simultaneously with its dispersion by the supercritical fluid, in a (conveniently) relatively large amount of a second vehicle specially chosen to be soluble in the supercritical fluid used for particle formation. On "mixing" of the substance and first vehicle, with the second vehicle, at their point of contact, hydrogen-bonding and/or similar interactions (eg. dipole-dipole interactions) are thought to form between molecules/ions of the first and second vehicles, such that on contact with the supercritical fluid, the relatively small amount of the first vehicle is able to dissolve into the supercritical fluid with the second vehicle, ie. the two vehicles may effectively be extracted together by the supercritical fluid to form a supercritical solution.

It is thus preferred that the flow rates of the two vehicles, on introduction into the particle formation vessel, be such as to create an excess of the second vehicle over the first at their moment of contact.

The advantage of the method of the invention is that it allows the preparation of particles, using a supercritical fluid technique, of substances which could not otherwise be used in such a technique because of their very low solubility in, or incompatibility with, the necessary solvents. It therefore considerably broadens the applications available for supercritical fluid particle formation techniques.

Moreover, because "mixing" of the two vehicles may occur substantially simultaneously with, or immediately prior to, dispersion and extraction by the supercritical fluid, a simple solution or suspension of the substance of interest in the first vehicle (for instance, an aqueous sugar or protein solution) may be introduced into the particle formation vessel, without the need to prepare complex two-vehicle systems beforehand.

This also means that the substance of interest need not be mixed with any incompatible vehicle(s) until immediately prior to, or at, particle formation. Thus, for instance, a hydrophilic protein may be introduced into the particle formation vessel in aqueous solution, and only comes into contact with the second (usually organic) vehicle at or just before the point of dispersion by the supercritical fluid, thus minimizing the risk of protein denaturing prior to particle formation.

The method of the invention also retains all the advantages of the method described in WO-95/01221. It provides the opportunity for manufacturing dry particulate products with highly controlled particle size and shape, by offering control over the working conditions, especially the pressure and temperature, at the exact point of particle formation. Such an improved control eliminates significant pressure fluctuation across the particle formation vessel and ensures a more uniform dispersion of the solution or suspension and the second vehicle by the supercritical fluid, resulting in a narrow size distribution for the fluid elements (eg. droplets) formed during the particle formation process. There is little or no chance that the dispersed fluid elements will reunite to form larger elements since the dispersion occurs by the action of the supercritical fluid itself, which also ensures thorough mixing of the solution or suspension and the second vehicle while rapidly removing the vehicles from the substance of interest to cause particle formation.

The simultaneous co-introduction of the solution or suspension, the second vehicle and the supercritical fluid, into a vessel inside which pressure and temperature are controlled, allows a high degree of control of operating parameters such as temperature, pressure and fluid flow rates, at the exact point when the fluids come into contact with one another and at the point of actual particle formation. Importantly, the supercritical fluid then acts both to disperse and to extract the two vehicles, as well as to ensure their thorough mixing. Because of this, controlling the relative flow rates of the fluids, into the particle formation vessel, allows accurate control over the size of the droplets (or other fluid elements) formed on dispersion of the vehicles, and hence of the particles formed substantially simultaneously by extraction of the vehicles into the supercritical fluid.

Through the pressure and temperature control, supercritical conditions are ideally maintained in the particle formation vessel at all times. The flow rate of the supercritical fluid relative to those of the other fluids, and its pressure and temperature, should be sufficient to allow the supercritical fluid to accommodate the vehicles (generally, the vehicles will represent no more than around 5% v/v of the supercritical fluid), so that it can extract them from the mixture and hence cause particle formation. Careful selection of such operating conditions ensures the existence of only a single supercritical phase during the entire particle formation process, allowing improved control over particle characteristics and substantially eliminating the risk of residual solvent in the particulate product.

Further advantages, for particles formed using a method according to the present invention, include good control over the quality of the crystalline and polymorphic phases, since the particles will all experience the same stable conditions of temperature and pressure when formed, as well as the potential for enhanced purity. This latter feature can be attributed to the high selectivity of supercritical fluids under different working conditions, enabling the extraction of one or more impurities from the vehicle containing the substance of interest.

Moreover, the co-introduction of the solution or suspension, the second vehicle and the supercritical fluid, leading to simultaneous dispersion and particle formation, allows particle formation to be carried out, if desired, at temperatures at or above the boiling point of either or both of the vehicles, which is something not possible using conventional particle formation techniques. This enables operation in temperature and pressure domains which were previously inaccessible, which in turn can allow the formation of products, or particular forms of products, that previously could not have been achieved. This, together with the high degree of control of the operating conditions made possible by the present invention, means that its uses could be extremely wide-ranging. Additionally its versatility would be of value in many fields.

The substance used in the method of the invention may be any substance which needs to be produced in particulate form. It typically (although not always) either is or comprises a substance which is soluble, or substantially soluble, only in solvents which are themselves substantially insoluble in the supercritical fluid chosen for use in the method, or which is incompatible with supercritical fluid-soluble solvents. Examples of such substances, where the supercritical fluid is carbon dioxide, may include lactose and other sugars, proteins, hydrophilic enzymes, inorganic materials (such as for use as dyestuffs), etc. However, it is to be understood that any substance from which particles are to be formed may be used in the method of the present invention.

In one particular embodiment of the invention, the substance from which particles are to be formed is for use in or as a pharmaceutical. However, the end product may, in fact, be any desired particulate product, for instance, a product of use in the ceramics, explosives or photographic industries; a foodstuff; a dye; etc. In each case, the principle behind the method of the invention remains the same; the technician need only adjust operating conditions in order to effect proper control over the substance being used.

The substance may be in a single or multi-component form (eg. it could comprise an intimate mixture of two materials, or one material in a matrix of another, or one material coated onto a substrate of another, or other similar mixtures). The particulate product, formed from the substance using the method of the invention, may also be in such a multi-component form—as described below, such products may be made from solutions or suspensions containing only single component starting materials, provided the solutions/suspensions are co-introduced with the supercritical fluid in the correct manner. The particulate product may also be a substance formed from an in situ reaction (ie. Immediately prior to, or on, dispersion by the supercritical fluid) between two or more reactant substances carried by the first and second vehicles.

The supercritical fluid may be any suitable supercritical fluid, for instance supercritical carbon dioxide, nitrous oxide, sulphur hexarfluoride, xenon, ethylene, chlorotrifluoromethane, ethane or trifluoromethane (again, this list is not exhaustive). A particularly preferred suoercritical fluid is carbon dioxide, due to its relative cheapness, non-toxicity, non-flammability and relatively low critical temperature.

The supercritical fluid may optionally contain one or more modifiers, for example, but not limited to, methanol, ethanol, isopropanol or acetone. When used, the modifier preferably constitutes not more than 20%, and more preferably constitutes between 1 and 10%, of the volume of the supercritical fluid.

The term "modifier" is well known to those persons skilled in the art. A modifier (or co-solvent) may be described as a chemical which, when added to a supercritical fluid, changes the intrinsic properties of the supercritical fluid in or around its critical point.

The first and second vehicles may be any appropriate vehicles, and may be chosen by the skilled man from within his general knowledge. The choice of vehicles in any particular case will depend on the nature of the substance from which particles are to be formed, on the supercritical fluid to be used in forming them, and on other practical criteria including those governing the desired end product. The choice of a suitable combination of supercritical fluid, modifier (where desired) and vehicles for any desired product will be well within the capabilities of a person of ordinary skill in the art.

The first vehicle is preferably one in which the substance is substantially soluble, but may itself be substantially insoluble in the chosen supercritical fluid. The second vehicle must be substantially miscible with the first, and substantially soluble in the chosen supercritical fluid. For example, where the substance is lactose and the supercritical fluid carbon dioxide, the first vehicle might be water and the second ethanol.

The two vehicles should be chosen on the basis of their polarities, functionalities and other considerations, so that, for instance, one vehicle contains functional groups that can hydrogen-bond with an acidic proton of the other vehicle, or can otherwise interact with functional groups contained in the other vehicle. Such interactions help to promote the extraction of the first vehicle into the supercritical fluid together with the second.

In the method of the invention, the substance of interest and the first vehicle may be substantially polar, the second vehicle then being substantially non-polar and both vehicles being substantially miscible in all proportions and preferably substantially soluble in the supercritical fluid.

In contrast, a substantially non-polar substance may be dissolved in a substantially non-polar first vehicle, the second vehicle then being substantially polar and both vehicles being substantially miscible in all proportions and preferably substantially soluble in the supercritical fluid.

These two sets of conditions are of particular use in a version of the invention in which the second vehicle acts as an anti-solvent for the substance of interest, ie. the substance is substantially insoluble in the second vehicle. This version of the invention will be described in more detail below.

It is to be understood that throughout this specification, the terms "first vehicle" and "second vehicle" each encompass a mixture of two or more fluids which together have the necessary solubilizing, miscibility and polarity characteristics.

As mentioned previously, there is preferably an excess of the second vehicle as the point of its contact with the first.

Typically, the amount of the first vehicle used will be the minimum possible to solvate the substance so as to create a single phase solution. This is preferably less than or equal to about 30%, more preferably less than or equal to about 10%, of the total amount of the first and second vehicles.

The amounts of the vehicles used, and their relative flow rates, may also depend on whether it is intended that some of the vehicle(s) remain in the final particulate product. For instance, if the first vehicle were water, then the amount used could affect whether the substance were precipitated in an anhydrous form, or in the form of its monohydrate, dihydrate, or whatever. Thus, the concentration of the first, or indeed the second, vehicle in the eventual mixture of vehicles, may be used to control "doping" of the final particulate product with vehicle "impurities". The invention allows a high degree of control over the residual vehicle content of the final particulate product.

In certain cases, the amount of the first vehicle (for instance, water) used may also determine which crystalline form of the substance is formed on treatment with the supercritical fluid.

In a preferred embodiment of the invention, the supercritical fluid, the solution or suspension, and the second vehicle are co-introduced into the particle formation vessel with concurrent directions of flow, more preferably with substantially coaxial directions of flow, such as by using a nozzle of coaxial design. Such a nozzle has an outlet end communicating with the interior of the particle formation vessel, and two or more coaxial passages which terminate adjacent or substantially adjacent to one another at the outlet end, at least one of the passages serving to introduce a flow of the supercritical fluid into the particle formation vessel, at least one of the passages serving to introduce a flow of the solution or suspension of the substance in the first vehicle, and at least one of the passages serving to introduce a flow of the second vehicle.

The nozzle is preferably of the type which allows "pre-filming" or "sheathing" of at least one of the fluids to occur, immediately prior to its contact with the other fluid(s). Note that this is not the same as creating a "jet" or "string" of one fluid to be broken up by another fluid. Ideally, the nozzle can be used to cause pre-filming of the solution or suspension and/or of the second vehicle, immediately prior to their dispersion by the supercritical fluid. This means that the dimensions of the nozzle passages, and the relative positions of their outlets, must be such that a fluid entering through one passage is formed, as it reaches the outlet of that passage, into a thin film or sheath of fluid, by its contact with, for example, the lip of an adjacent passage outlet. This film or sheath can then be stretched, and ultimately dispersed into separate fluid elements, when it comes into contact with an oncoming stream of the supercritical fluid in another nozzle passage. Clearly, the thickness of the film or sheath, and hence the sizes of the fluid elements formed on dispersion, will depend to a large extent on the relative flow rates of the fluids, and also on the nozzle passage dimensions.

The use of such an inlet device ensures no contact between the formed particles and the vehicles around the nozzle tip area. Contact would reduce control of the final product size and shape. Extra control over the size of the dispersed vehicle fluid elements, in addition to that provided by the nozzle design, may be achieved according to the first aspect of the invention by controlling the flow rates of the supercritical fluid, the solution/suspension and the second vehicle into the particle formation vessel. At the same time, the ability to retain the formed Particles in the vessel eliminates the potential for contact with the vehicles that might otherwise take place on eventually depressurizing the supercritical solution. Such contact would affect the shape and size, and potentially the yield, of the product.

Preferably, the opening at the outlet end (tip) of the nozzle will have a diameter in the range of 0.05 to 2 mm, and more preferably between 0.1 and 0.3 mm, typically about 0.2 mm. The angle of taper of the outlet end (with respect to the main axis of the nozzle) will depend on the desired velocity of the fluids introduced through the nozzle; a change in the angle may be used, for instance, to increase the velocity of the supercritical fluid and hence to increase the amount of physical contact between the supercritical fluid and the vehicles. Typically (although not necessarily), the angle of taper will be in the range of about 10° to about 60°, preferably between about 10° and 50°, more preferably between about 20° and about 40°, and most preferably about 30°. The nozzle may be made of any appropriate material, for example stainless steel.

In one embodiment of the invention, the nozzle has three coaxial passages, an inner, an intermediate and an outer. This design allows both vehicles, and the supercritical fluid, to be introduced separately into the particle formation vessel. However, the nozzle may have any appropriate number of coaxial passages, some of which may be used to introduce additional reagents into the particle formation vessel. One or more of the passages may be used to introduce two or more fluids at the same time, and the inlets to such passages may be modified accordingly.

The solution or suspension of the substance in the first vehicle may be introduced through one nozzle passage, and the supercritical fluid and the second vehicle may be introduced together through another passage. Mixing of the two vehicles then occurs simultaneously with their dispersion and extraction by the supercritical fluid. This may be effected using a two-passage nozzle or, using a nozzle having three or more passages, the solution or suspension may be introduced between an inner and an outer flow of the supercritical fluid/second vehicle mixture, which improves dispersion and mixing by exposing both sides of the solution/suspension to the supercritical fluid and second vehicle.

The internal diameters of the coaxial passages may be chosen as appropriate for any particular case. Typically, for a three-passage nozzle, the ratio of the internal diameters of the outer and the inner passages may be in the range of from 2 to 5, preferably between about 3 and 4. The ratio of the internal diameters of the outer and intermediate passages may be in the range of from 1.2 to 3, preferably between about 1.4 and 1.8.

Examples of such coaxial nozzles, and their typical dimensions, are illustrated in FIGS. 3 and 4.

The temperature in the particle formation vessel may be maintained at a desired level (preferably ±0.1° C.) by means of a heating jacket or, more preferably, an oven. The pressure in the particle formation vessel is conveniently maintained at a desired level (preferably ±2 bar at 350 bar) by means of an automated back-pressure regulator. It will be appreciated that such apparatus will be readily available from, for example, manufacturers of supercritical fluid extraction equipment, for instance, from Jasco Inc., Japan.

Control of parameters such as size, size distribution, shape and crystalline form in the particulate product will be dependent upon the operating conditions used when carrying out the method of the invention. Variables include the flow rates of the supercritical fluid and/or the solution or suspension and/or the second vehicle, the relative amounts of the two vehicles, the concentration of the substance in the first vehicle, and the temperature and pressure inside the particle formation vessel.

It will also be appreciated that the precise conditions of operation will be dependent upon the choice of supercritical fluid and whether or not modifiers are present. Table 1, for instance, lists, the critical pressures and temperatures for some selected fluids:

TABLE 1

| Fluid | Pc (bar) | Tc (° C.) |
|---|---|---|
| carbon dioxide | 74 | 31 |
| nitrous oxide | 72 | 36 |
| sulphur hexafluoride | 37 | 45 |
| xenon | 58 | 16 |
| ethylene | 51 | 10 |
| chlorotrifluoromethane | 39 | 29 |
| ethane | 48 | 32 |
| trifluoromethane | 47 | 26 |

In practice, it may be preferable to maintain the pressure inside the particle formation vessel substantially in excess of the Pc (for instance, 100–300 bar for carbon dioxide) while the temperature is only slightly above the Tc (e.g. 40–60° C. for carbon dioxide).

The flow rates of the supercritical fluid and/or the solution or suspension and/or the second vehicle, into the particle formation vessel, may be controlled so as to achieve a desired particle size, size distribution, shape and/or form. Typically, the ratio of the solution/suspension flow rate to the supercritical fluid flow rate will be between 0.001 and 0.2, preferably between 0.001 and 0.1, more preferably between 0.01 and 0.07, and most preferably around 0.03. The flow rate of the supercritical fluid, relative to those of the other fluids, is particularly important because the supercritical fluid acts to disperse the two vehicles. Its flow rate therefore affects the size of the droplets or other fluid elements caused by the dispersion, and hence of the particles formed by extracting the vehicles from those fluid elements.

The method of the invention preferably additionally involves collecting the particles following their formation, more preferably in the particle formation vessel itself. The method may also involve recovering the supercritical solution formed on extraction of the vehicles into the supercritical fluid, separating the components of the solution and recycling one or more of those components for future use.

The method is preferably carried out in a substantially continuous, as opposed to batch-wise, manner. Apparatus which can be used to carry out the process continuously is described below.

According to one particular version of the method of the invention, the substance of interest is only sparingly soluble, if at all, in the second vehicle. The second vehicle thus acts as an antisolvent for the substance, and on contact of the second vehicle with a solution of the substance in the first vehicle, the second vehicle causes precipitation of the substance from its solution.

In this case, the second vehicle may contain a "seed" of the substance of interest, or indeed of any other suitable material (insoluble in the second vehicle), to induce nucleation of the substance of interest when the second vehicle comes into contact with the solution or suspension of the substance in the first vehicle. The seed may be, for example, a pharmaceutically acceptable carrier where the substance of interest is for use in or as a pharmaceutical, or it may itself be a pharmaceutically active material, to be coated with a substance, such as a taste-masking agent, which is precipitated out of the first vehicle onto the seed.

When carrying out this version of the invention, the various fluids must be introduced into the particle formation vessel in such a way that the second vehicle, and the solution or suspension of the substance of interest in the first vehicle, contact one another before, and preferably shortly or immediately before, their contact with and hence dispersion and extraction by the supercritical fluid. The second vehicle comes into contact with the solution or suspension, and dramatically increases the supersaturation ratio of the resultant mixture, causing nucleation and the formation of embryos or nucleation sites, which can act as centers of crystallization for the substance of interest. After this preferably immediately, the mixture is dispersed by the supercritical fluid, and simultaneously the two vehicles are rapidly extracted into the supercritical fluid, leading to the formation of a dry particulate product.

Dispersion of the mixture of vehicles, which already contains growing particle embryos, into fluid elements by the supercritical fluid allows a high level of control over the growth of the particles and hence over their ultimate size. By controlling parameters such as the flow rates of the solution or suspension, the second vehicle and the supercritical fluid, and the temperature and pressure inside the particle formation vessel, it is possible to control the size and size distribution of the particles formed, as well as their shape, morphology and other characteristics, to a great degree of accuracy.

When the solution or suspension of the substance in the first vehicle is contacted with the second vehicle, and the mixture is dispersed by the supercritical fluid, the second vehicle "diluent" alters the polarity of the resultant supercritical solution. This can minimize extraction of the substance by the supercritical solution and hence enhance the yield of the particulate product. The mixing ratio of the second vehicle with the solution or suspension of the substance of interest, should ideally be kept slightly below the supersaturation ratio of the solution/suspension, in particular, when the two are mixed just before dispersion, because the second vehicle, acting as an anti-solvent for the substance of interest, can cause precipitation of the substance and eventual blocking of the nozzle or other inlet to the particle formation vessel.

Because of the need for the second vehicle to act as an anti-solvent for the substance, it is virtually essential in this version of the invention that the two vehicles have very different polarities. Thus, for instance, the substance and the first vehicle may be substantially polar, while the second vehicle is substantially non-polar, or vice versa.

Again in this version, the two vehicles are preferably both substantially soluble in the chosen supercritical fluid, and the second vehicle must be substantially miscible with the first in all proportions.

Such a version of the method is preferably carried out using a coaxial nozzle, as described above, as the means for co-introducing the various fluids into the particle formation vessel. The nozzle can have at least three coaxial passages, to allow the separate introduction of the solution or suspension, the second vehicle and the supercritical fluid, and to allow their contact with one another at the appropriate times. The outlet of at least one of the inner nozzle passages should be located a small distance upstream (in use) of the outlet of at least one of its surrounding passages. This allows a degree of mixing to occur, between the solution or suspension and the second vehicle, (and hence also a degree of particle precipitation) within the nozzle—the solution or suspension and the second vehicle are introduced through the inner passage and surrounding passage in question. The supercritical fluid may then be introduced through an outer passage (ie. one surrounding the two passages already mentioned), and will contact the mixture, causing dispersion and extraction to occur, downstream of the initial point of mixing. The relative flow rates of the fluids will determine how soon after mixing the two vehicles will be dispersed by the supercritical fluid; typically, very short time intervals will be desired.

A nozzle having more than three coaxial passages may, of course, be used in this version of the invention. For instance, a nozzle having four or more passages may be used to introduce the solution or suspension and the second vehicle (and preferably to cause their pre-filming), between an inner and an outer flow of the supercritical fluid, for instance one through the innermost and one through the outermost passage of a four passage nozzle. Again, the outlet of the inner of the two passages carrying the solution/suspension and the second vehicle must terminate slightly upstream of the outlet of the outer of these two passages, to allow pre-mixing of the solution/suspension and the second vehicle to take place.

In an alternative version of the method of the invention, the solution or suspension of the substance in a relatively small amount of the first vehicle may be added to a relatively large amount of (ie. "diluted in") the second vehicle, prior to the co-introduction of the mixture into a particle formation vessel with a supercritical fluid. This may be done where there is no incompatibility between the substance of interest and the two vehicles. Thus, in its broadest aspect, the invention simply involves the use of the first and second vehicles to carry the substance of interest, and the co-introduction of the vehicles and substance into a particle formation vessel (the temperature and pressure in which are controlled) with a supercritical fluid, in such a way that dispersion of the solution or suspension and the second vehicle, and extraction of the vehicles, occur substantially simultaneously and substantially immediately on introduction of the fluids into the particle formation vessel, by the action of the supercritical fluid. Again, the two vehicles "mix" and are extracted together into the supercritical fluid.

Clearly, such a method can be carried out in the same manner as is described above. In particular, an excess of the second vehicle is preferably used, relative to the amount of the first vehicle used.

According to a second aspect of the present invention, there is provided apparatus for use in carrying out a method according to the first aspect, the apparatus comprising a particle formation vessel; means for controlling the temperature in the vessel at a desired level; means for controlling the pressure in the vessel at a desired level; and means for the co-introduction, into the vessel, of the supercritical fluid, the solution or suspension of the substance in the first vehicle, and the second vehicle, in such a way that contact between the solution or suspension and the second vehicle occurs either substantially simultaneously with, or immediately before, dispersion of the solution or suspension and the second vehicle by the action of the supercritical fluid and extraction of the vehicles by the supercritical fluid, and such that the dispersion and extraction occur substantially simultaneously and substantially immediately on introduction of the fluids into the particle formation vessel.

In general, apparatus for use in carrying out the method of the invention may comprise any suitable means for co-introducing the fluids into the particle formation vessel. However, according to the second aspect of the invention, the means for the co-introduction of the fluids into the vessel comprises a nozzle having an outlet end communicating with the interior of the vessel, and at least three (preferably three or four) coaxial passages which terminate adjacent or substantially adjacent to one another at the outlet end, at least one of the passages serving to introduce a flow of the supercritical fluid into the vessel, at least one of the passages serving to introduce a flow of the solution or suspension and at least one of the passages serving to introduce a flow of the second vehicle, all fluid flows being in substantially coaxial directions, and wherein the outlet of at least one of the inner nozzle passages is located a small distance upstream (in use) of the outlet of one of its surrounding passages so as to allow, in use, a degree of mixing to occur within the nozzle, between the solution or suspension and the second vehicle, when the solution/suspension and the second vehicle are introduced through the inner passage and surrounding passage in question.

It will be appreciated that, where necessary, such apparatus may additionally comprise means for the collection of the particulate product, for example, means, such as a filter, for the retention of the product in the particle formation vessel, thus to reduce loss of the product together with the supercritical solution also formed. An alternative particle collection means may involve a cyclone separating device.

The apparatus may include means for recovering the supercritical solution formed on extraction of the vehicles into the supercritical fluid; means for separating the components of the supercritical solution; and optionally means for recycling one or more of those components back into the apparatus for future use, so as to increase its overall efficiency.

It will be further appreciated that the apparatus may comprise more than one particle formation vessel and/or means for the collection of the particulate product, thereby allowing for the substantially continuous operation of the apparatus through simple switching from one particle formation vessel or collection means to another as required Such adaptation for continuous operation represents a further embodiment of the present invention.

The means for controlling the temperature and pressure in the particle formation vessel preferably comprise an oven and an automated back-pressure regulator respectively, although other appropriate, known means may be used.

An advantage of apparatus according to the invention is that it can allow particle formation to occur in a completely closed environment, ie. in a closed particle formation vessel. The apparatus can be sealed from the atmosphere, making it easy to maintain sterile operating conditions and reducing the risk of environmental pollution, and it can also be kept free of oxygen, moisture or other relevant contaminants. The particle formation vessel can also easily be made light-free, of particular use for the preparation of photosensitive products such as for use in the photographic industry.

According to a third aspect of the present invention, there is provided a particulate product made using the method of the first aspect of the invention and/or the apparatus of the second aspect.

DETAILED DESCRIPTION OF THE PREFERRED EXEMPLARY EMBODIMENTS

FIGS. 1–4 illustrate apparatus which may be used to carry out a method in accordance with the present invention, ie. for the formation of particles. The subsequent examples illustrate how the invention has been carried out, in order to prepare particulate products of various substances.

Figure 1:
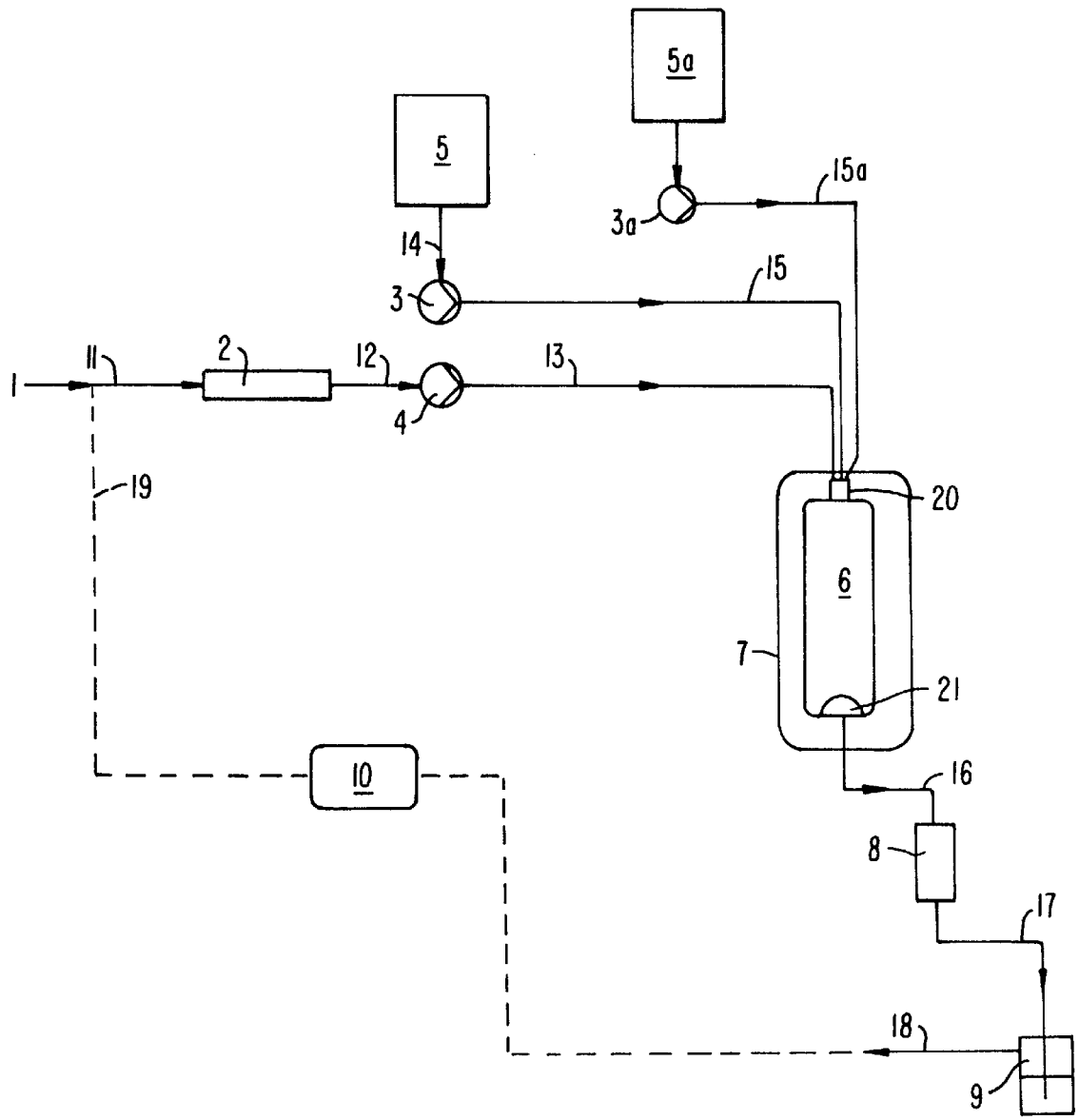
FIG. 1 is a schematic showing apparatus for use in carrying out a method in accordance with the first aspect of the invention.
Figure 2A:
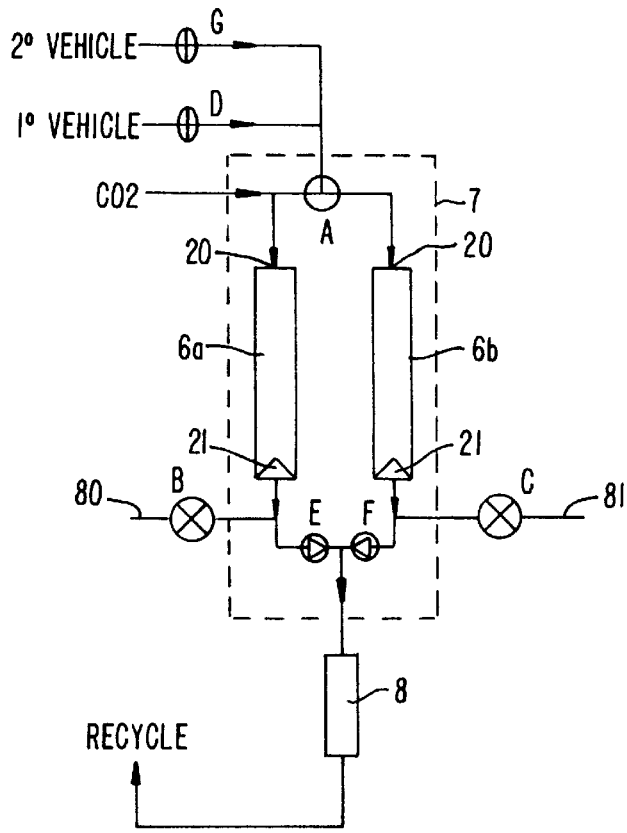
FIGS. 2A and 2B show schematic designs of alternative sets of apparatus for the same purpose.
Figure 2B:
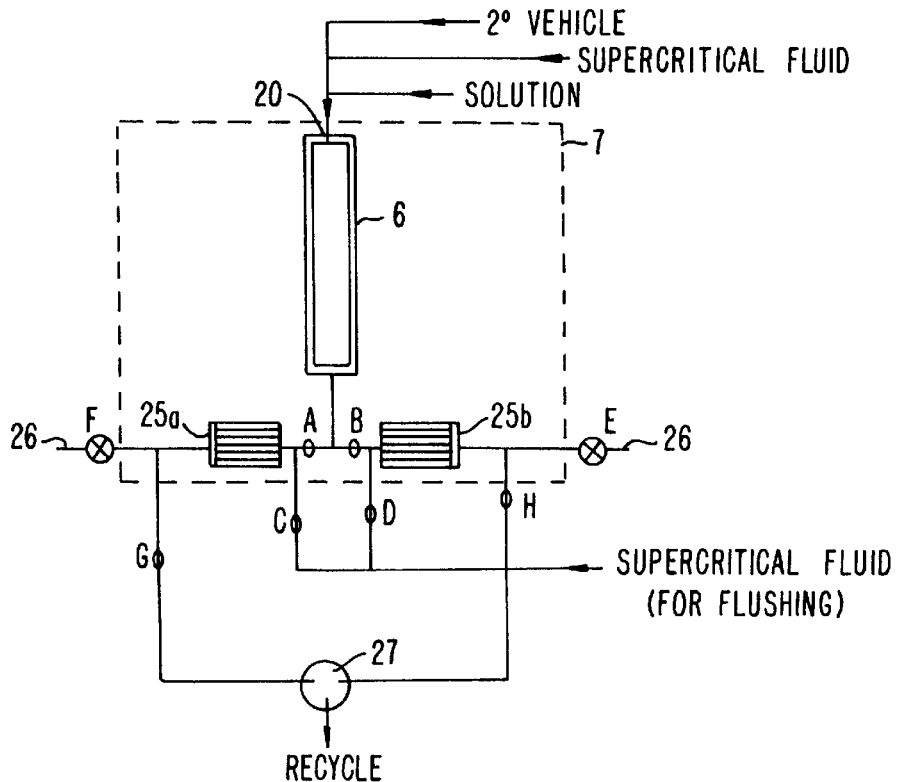
Figure 3:
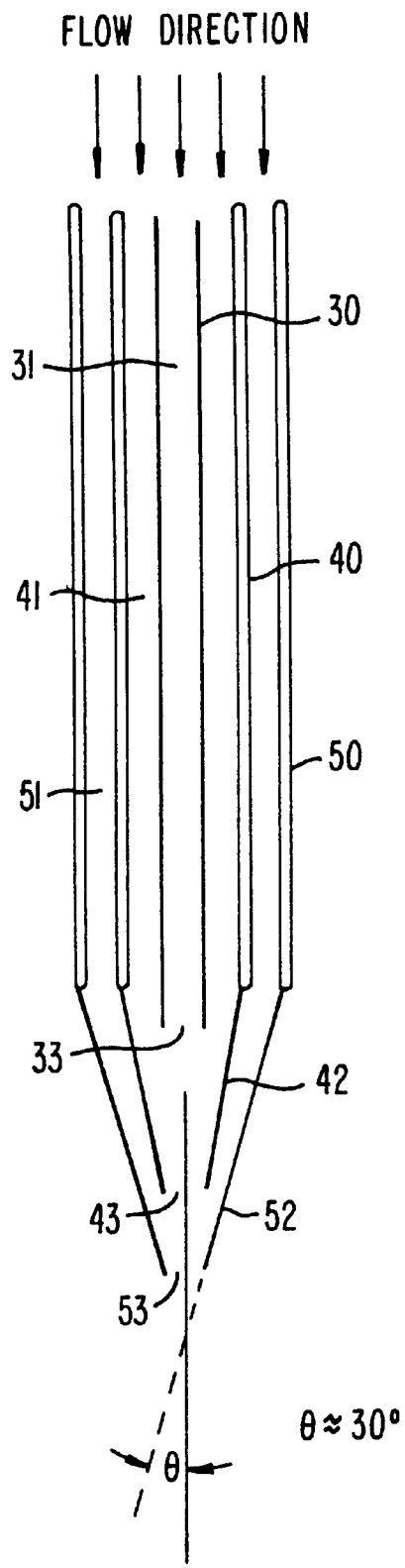
FIG. 3 is a longitudinal section through the outlet end of a coaxial nozzle for use in the apparatus of FIG. 1, FIG. 2A or FIG. 2B.
Figure 4A:
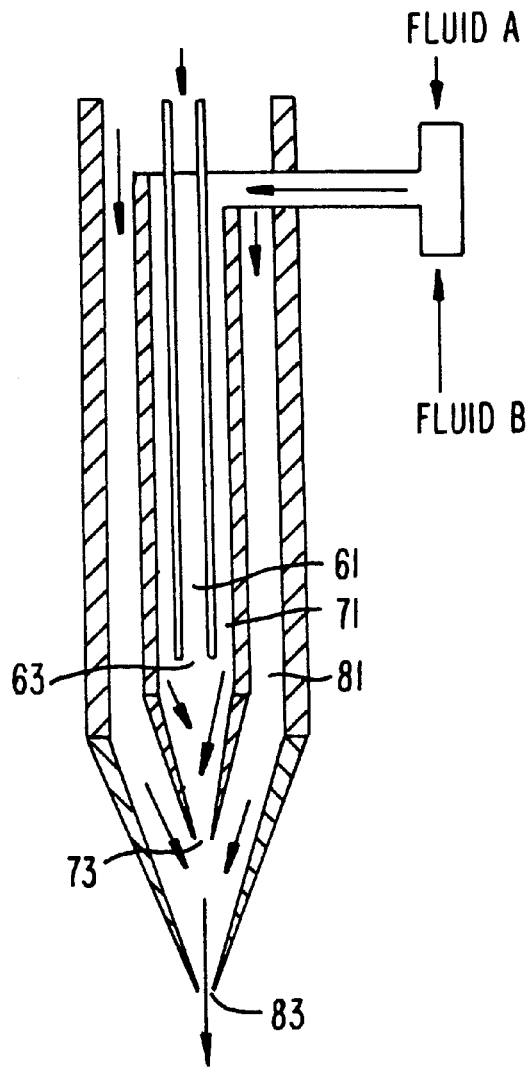
FIGS. 4A and 4B are a longitudinal and a transverse section respectively through the outlet end of an alternative coaxial nozzle for use in the apparatus of FIG. 1, FIG. 2A or FIG. 2B.
Figure 4B:
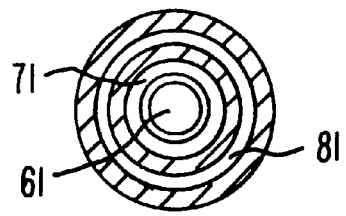

FIGS. 1, 2A and 2B are simplified diagrammatic flow sheets of apparatus of use in carrying out the invention, and FIGS. 3 and 4 show nozzles which may be used in such apparatus.

Referring to FIG. 1, the apparatus shown includes a particle formation vessel 6. This is typically a standard reaction vessel, for instance of the type available from Keystone Scientific Inc., of an appropriate capacity for the particular use to which it is to be put. The temperature and pressure in the vessel are maintained at a constant desired level, by means of an oven 7 and back-pressure regulator 8 (eg. model number 880-81 of Jasco Inc.) respectively.

In use, the system is initially pressurized and stable working conditions are met. A suitable gas, for example, carbon dioxide, is fed from source 1 via conduit 11 to a cooler 2, to ensure liquification, and is fed by conduit 12 to a pump 4. From there, it is fed by conduit 13 to the vessel 6 via a nozzle 20. A solution of a solid of interest, for example, lactose, in a suitable first vehicle, for example water, is drawn from source 5 by a conduit 14 to a pump 3 and is fed by conduit 15 to the vessel 6 via nozzle 20. A second vehicle, for example, ethanol, is fed from source 5a to nozzle 20 via conduit 15a and pump 3a.

The nozzle 20 allows the fluids to be co-introduced into the vessel 6, and may be as shown in FIG. 3 or FIG. 4. The nozzle of FIG. 3 comprises three coaxial tubes 30, 40 and 50 which define an inner passage 31, an intermediate passage 41 and an outer passage 51 respectively. Tubes 40 and 50 have conically tapering end portions 42 and 52, the angle of taper of the end portion 52, θ, relative to the main axis of the nozzle, being about 30° in this (non-limiting) example. The end of tube and the tips of the end portions 42 and 52 define respective orifices 33, 43 and 53, with the orifices 43 and 53 being a short distance downstream of the orifice 33.

In use of the nozzle, fluids introduced through the inner and intermediate passages 31 and 41 are "pre-filmed" prior to their contact with a fluid introduced through the outer passage 51. In other words, because of the shapes and dimensions of the nozzle passages, and the relative positions of their outlet orifices, fluids reaching the orifices 33 and 43 are formed into thin fluid films, which may then be stretched, and ultimately broken up into individual fluid elements, by a fluid flowing through the outer passage 51.

The nozzle of FIG. 3 allows three fluids to be co-introduced into the vessel 6. For instance, a solution or suspension of the substance of interest in the first vehicle may be introduced through the inner passage 31, the second vehicle through the intermediate passage 41 and the supercritical fluid through the outer passage 51. "Mixing" of the solution or suspension and the second vehicle, and their filming, then occurs immediately prior to their dispersion by the supercritical fluid between orifices 43 and 53. It is also possible to add, through one of the three passages, a desired carrier or other additive intended to form part of, or be mixed with, the final particulate product. The additive is then dispersed simultaneously with the substance of primary interest. Also, in situ reactions may be carried out immediately prior to, or on, dispersion by the supercritical fluid, by introducing two or more reactants in two separate vehicles through two of the nozzle passages, the reaction occurring at the passage outlets either immediately prior to, or on, dispersion.

In the nozzle shown, inner tube 30 has an internal diameter of 0.25 mm; intermediate tube 40 has an internal diameter of 0.53 mm; and outer tube 50 has an internal diameter of 0.8 mm and an outside diameter of 1.5 mm. The tip opening (53) has an internal diameter of 0.2 mm. The tubes are all made of stainless steel.

However, the nozzle may be made of any appropriate material and have any suitable dimensions. For instance, the internal diameters of the tubes may be in the ranges 0.05–0.35 mm (inner); 0.25–0.65 mm (intermediate); and 0.65–0.95 mm (outer), preferably between 0.1 and 0.3 mm (inner); 0.3 and 0.6 mm (intermediate); and 0.7 and 0.9 mm (outer). The tip opening 53 is likely to have an internal diameter in the range 0.1–0.3 mm, preferably between 0.18 and 0.25 mm.

An alternative form of coaxial nozzle, again for use in the apparatus of FIGS. 1 and 2 and which again causes "pre-filming" of fluids in its inner passages, is shown in FIGS. 4A and 4B. This nozzle has three coaxial passages, an inner 61, an intermediate 71 and an outer 81. Their outlet orifices are, respectively, 63, 73 and 83, orifices 63 and 73 being a short distance upstream, in use, of the orifice 83. The in-use direction of fluid flow is indicated by the arrows.

The inlet to the intermediate passage 71 is modified by the inclusion of a T-shaped tube 89, which allows the introduction into the passage of two separate fluids, labelled Fluid A and Fluid B in FIG. 4A. These may be, for instance, (A) a solution/suspension of a substance in a first vehicle and (B) a second vehicle, in which case a supercritical fluid might then be introduced through passages 61 and 81 of the nozzle. Alternatively, Fluids A and B might each be a solution or suspension of a reactant material, allowing the in situ (ie. in nozzle passage 71) formation of a desired product of the two reactants, which product can then be produced in particulate form on contact with a supercritical fluid introduced through outer passage 81. Clearly, the use of such a modified nozzle greatly increases the versatility of the apparatus of FIGS. 1 and 2, allowing a variety of different fluid types to be introduced into the particle formation vessel in different combinations.

The dimensions for the FIG. 4 nozzle are as described above in relation to the nozzle of FIG. 3.

Using the apparatus of FIG. 1, the supercritical fluid may be fed under pressure (ie. at a high flow rate when compared with the flow rates of the solution/suspension and the second vehicle) through, for example, the outer nozzle passage 51 of the nozzle shown in FIG. 3 (81 in FIG. 4); the solution or suspension of the solid of interest in a first vehicle may be simultaneously fed under pressure through the inner passage 31 (61); and a second vehicle may be introduced through the intermediate passage 41 (71). It is believed that the high velocity supercritical fluid emerging from the passage 51 causes the fluids emerging from the ends of passages 31 and 41 to be broken up into fluid elements (eg. droplets) from which the vehicles are substantially simultaneously extracted by the supercritical fluid to result in the formation of particles of the solid previously held in the first vehicle. It is to be understood, however, that although it is believed that this is what occurs, we do not wish to be bound by this theoretical explanation, and the actual physical processes occurring may not be precisely as just indicated.

Also, although a configuration has been described in which the supercritical fluid passes through the outer passage 51, the first vehicle through inner passage 31 and the second vehicle through intermediate passage 41, the configuration may be altered if appropriate, and any one of the three passages, of the nozzle of either FIG. 3 or FIG. 4, may be used to carry any one of a number of desired fluids. Similarly, a nozzle having a different number of coaxial passages, or of a different overall type, may be used in the FIG. 1 apparatus.

The nozzle 20 ensures dispersion of the vehicles by the shearing action of the high velocity supercritical fluid, and also thorough mixing of the dispersed vehicles with the supercritical fluid which simultaneously extracts the vehicles from the dispersed liquid, resulting in substantially immediate particle formation of the solid of interest. Because, using the FIG. 3 or FIG. 4 nozzle, the supercritical fluid and vehicles are introduced coaxially, and dispersion occurs substantially simultaneously with vehicle extraction. At the entrance to a vessel in which temperature and pressure are carefully controlled, a very high degree of control is possible of the conditions (e.g. pressure, temperature and flow rates) affecting particle formation at the exact time when it occurs. The coaxial introduction also allows both vehicles to be extracted into the supercritical fluid together, even if the first vehicle is substantially insoluble in the supercritical fluid.

The particles formed are retained in the particle formation vessel by collecting means 21. The resultant supercritical solution is fed by conduit 16 to a back-pressure regulator 8 and is then fed by conduit 17 to a separation vessel 9 where it expands to cause the supercritical fluid to separate as a gas from the liquid vehicles. The gas may be fed by conduit 18 to a tank 10 and returned by conduit 19 to the cooler 2. The vehicles may also be collected for subsequent re-use. Means, not shown, may be provided to smooth the fluid flow pulse produced by pumps 3, 3*a* and 4, so as to eliminate, or at least reduce, any flow pulsations.

When sufficient particle formation has occurred in the vessel 6, it is flushed through with clean, dry supercritical fluid, so as to ensure removal of any residual vehicle. The vessel can then be depressurized and the particulate product removed.

The alternative apparatuses shown schematically in FIGS. 2A and 2B are for use in continuous particle formation. That shown in FIG. 2A includes two particle formation vessels 6a and 6b, each of the type shown in FIG. 1 and each including an inlet nozzle 20, as described above, and a particle collecting means (such as a filter) 21. Oven 7 and back-pressure regulator 8 serve both vessels.

In the apparatus of FIG. 2A, valve A controls the supply of the supercritical fluid, the first vehicle (containing the substance of interest) and the second vehicle to the two vessels 6a and 6b, and one-way valves E and F control the outlets from the two vessels to the back-pressure regulator 8. Valves D and G control the supply of the two vehicles to valve A. Valves B and C are needle valves, and items 80 and 81 are vents.

The apparatus may be "continuously" operated as follows. Valve A is firstly set to supply fluids to vessel 6a, in which particle formation is allowed to occur, as described in connection with FIG. 1 Valve E is set so that the resultant supercritical solution may drain from vessel 6a to the back-pressure regulator 8 for subsequent recycling.

When sufficient particle formation has occurred, valves D and G are closed to stop the flow of vehicles, while the supercritical fluid continues to flow through vessel 6a to dry (flush) the product. Valve A is then set to supply fluids to the empty vessel 6b, and valves D and G re-opened, while valve B is opened so as slowly to depressurize vessel 6a. One-way valve E eliminates any chance of a back-flow from vessel 6b or of disruption of the particle formation process now occurring in vessel 6b. Vessel 6a is removed for collection of the product, and then refitted and re-pressurised ready for re-use. Supercritical solution drains from vessel 6b via valve F, which is set appropriately.

Once particle formation in vessel 6b is complete and, the valves are set back to allow it to continue in vessel 6a, while 6b is flushed and emptied. In this way, particle formation in the apparatus can continue uninterrupted.

The apparatus shown in FIG. 2B includes only one particle formation vessel 6, which does not contain any particle collecting means, and two particle collection vessels 25a and 25b downstream of vessel 6. In use, the supercritical solution carries the formed particles to the collection vessels 25a and 25i b.

The apparatus also includes an inlet nozzle 20, preferably as described above, two vents 26, a back pressure regulator 27, an oven 7 and valves A–H. Supercritical fluid, solution or suspension (of substance in first vehicle) and second vehicle are fed to the nozzle 20 where shown.

The apparatus might be used as follows. Initially, (valves C,D,E and F closed) the system is pressurized and stable working conditions are met; valves B and H are then closed, driving the flow of supercritical fluid through valve A only. The supercritical fluid, the solution/suspension of the first vehicle and substance of interest and the second vehicle are introduced into vessel 6 and the particles formed are transported by the resultant supercritical solution, via valve A. to collection vessel 25a which contains a particle retention device. The retention device is placed at the outlet of the vessel to ensure maximum collection volume. The solid-free supercritical solution (the supercritical fluid and the vehicles) flows across valve G to the back pressure regulator 27. On emerging from the back pressure regulator, the supercritical solution expands into a large pressure resistant vessel (not shown), where the vehicles separate from the gas and both can be recycled.

When the collection vessel 25a is full, switching takes place, closing valves A and G and simultaneously opening valves B and H. This allows the flow of the supercritical solution, emerging from vessel 6, into the second collection vessel 25b. Valves C and G are opened after flow switching to ensure a high flow of supercritical fluid to flush the full collection vessel 25a, i.e. the supercritical solution volume is replaced by a supercritical fluid volume. It is estimated that 1–2 times the volume of the collection vessel, of supercritical fluid, ensures a dry powder. The flushing time is generally short because the particles themselves are occupying the volume of the collection vessel. After flushing, valves C and G are closed and valve F (a needle valve) is slowly opened to depressurize the full collection vessel 25a. Since the particulate product takes up the vessel volume, only a small amount of supercritical fluid is discharged, mainly the internal volume of the fittings involved.

The full collection vessel 25a is removed and the dry powder collected. After refitting and repressurizing via valve C, the vessel is ready for re-use as soon as the second collection vessel 25b, which has meanwhile been collecting product from vessel 6, is full.

The benefits of using the apparatus of FIG. 2B include:
1. The elimination of depressurizing and pressurizing steps of the particle formation vessel every time product is collected. This could mean considerable reductions in the amounts of fluids being discharged, in particular, when using a large volume particle formation vessel (scaling up) or expensive high purity fluids.
2. Significant time saving during the flushing (drying) procedure. In a batch particle formation process, only a rather small volume of the reaction vessel is occupied by the product and the remaining volume (where dispersion takes place) is taken up by the supercritical solution. This mixture will eventually be replaced by at least the same volume of supercritical fluid in the flushing procedure, which can therefore take a long time when scaled up.
3. The environment and workers are less exposed to the products during the recovery step. It can be difficult to collect products directly from a large reaction vessel due to handling inconvenience or because the products of interest are light, oxygen or humidity sensitive which might affect their characteristics or purity.

It is to be understood that the apparatus of either FIG. 2A or 2B may be used to carry out the method of the present invention.

The invention will now be further illustrated by the following non-limiting examples.

EXAMPLES

The following examples were carried out using a method according to the present invention, and apparatus generally similar to that shown in FIGS. 1–4. They illustrate the versatility of the method of the invention, its usefulness in forming particles of materials which would otherwise be difficult to prepare by supercritical fluid techniques and the advantageous effects which can thereby be achieved.

Examples 1 & 2

Formation of Lactose Particles

The following examples illustrate the successful and controlled formation of crystalline lactose, using carbon dioxide as a supercritical fluid, despite the very low solubility of lactose in conventional $CO_2$-soluble organic solvents. According to the present invention, two vehicles were used for the lactose, water as the first and an organic solvent (methanol), which is miscible with water and soluble in supercritical carbon dioxide, as the second.

Example 1
Preparation of Lactose (I)

In accordance with the invention, a solution of lactose in a relatively small amount of water and a relatively large amount of a second vehicle, methanol, was used. The solution was co-introduced, with supercritical $CO_2$, into a particle formation vessel of the type shown in FIGS. 1 and 2, through a three-passage nozzle of the type shown in FIG. 3. The pressure and temperature inside the vessel were carefully maintained at the desired operating levels throughout particle formation. It is thought that the miscible water and methanol were extracted together into the supercritical $CO_2$, despite the insolubility of water in tne supercritical fluid.

Figure 5:
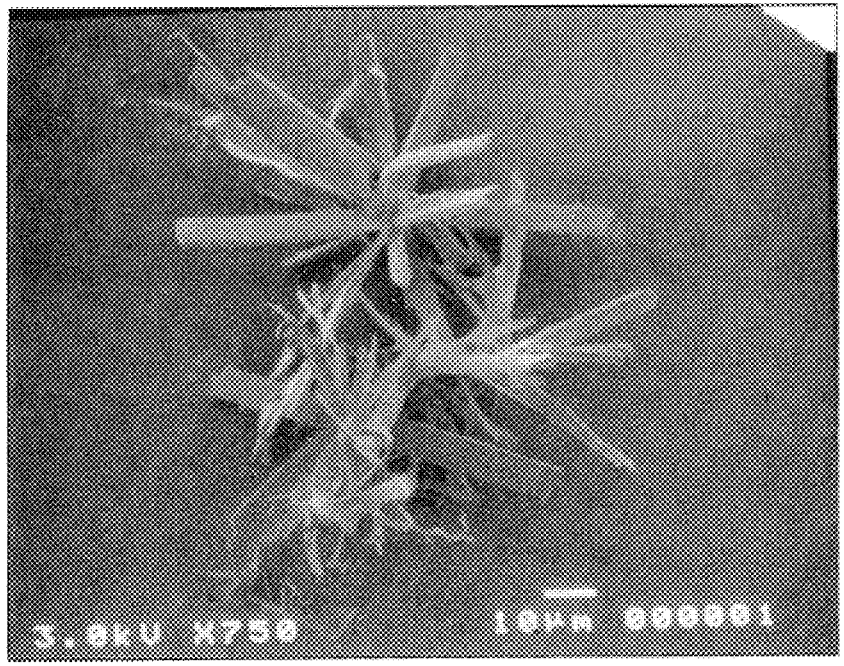
FIG. 5 is an SEM (scanning electron microscope) micrograph of lactose prepared according to Example 1.
Figure 6:
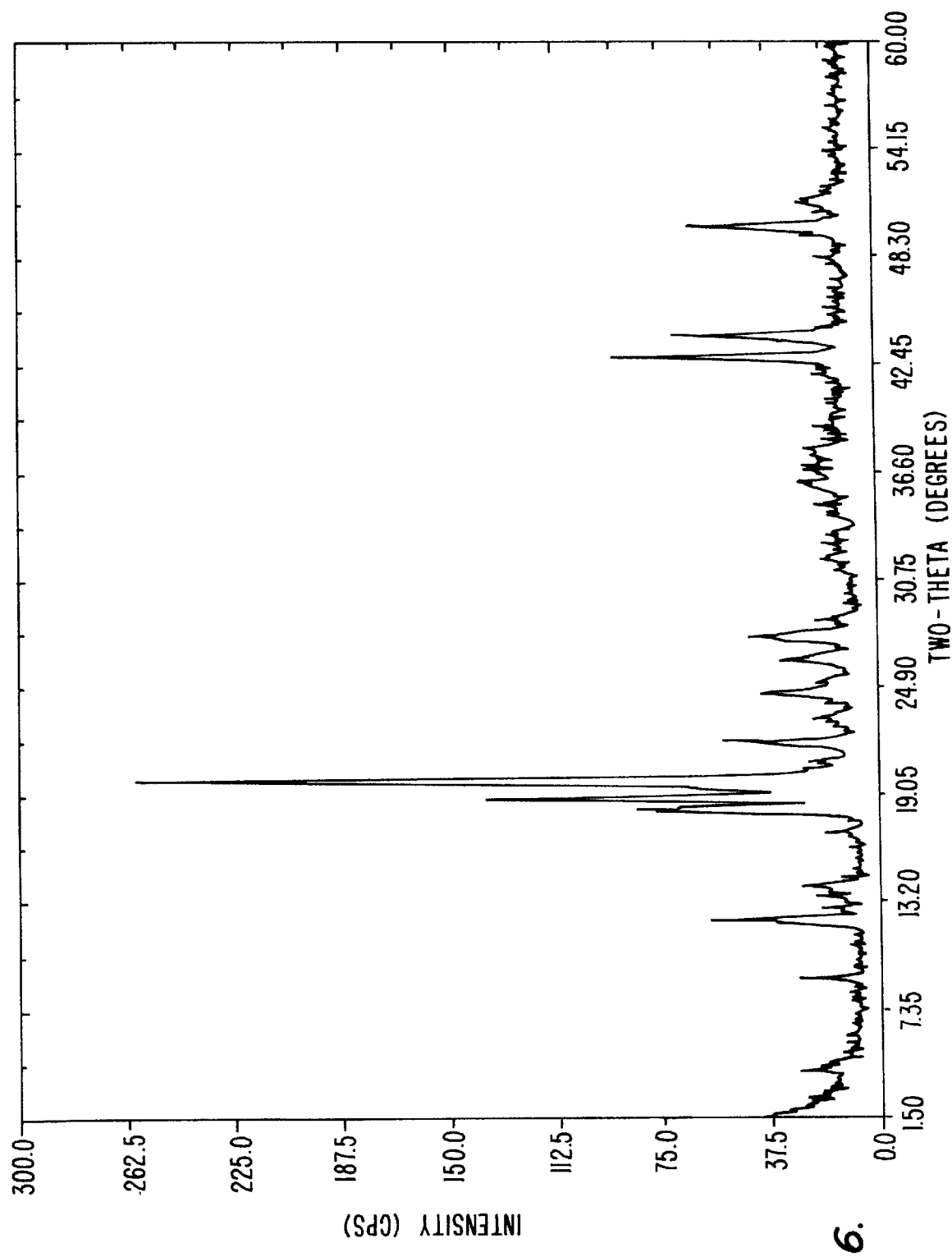
FIG. 6 is an XRD (X-ray diffraction) pattern for the sample shown in FIG. 5.

0.3 g of alpha-lactose monohydrate was dissolved in 2 ml deionized water, 98 ml of methanol was added to the aqueous solution and the mixture was introduced into the 32 ml particle formation vessel through the three-passage nozzle. The operating conditions were 270 bar and 70° C. inside the vessel, a solution flow rate (in the intermediate nozzle passage) of 0.5 ml/min and a supercritical $CO_2$ flow rate (in the inner and outer passages) of 7.5 ml/min. The product (a fine white powder) was collected at the end of the experiment. An SEM micrograph and XRD pattern for the product are shown in FIGS. 5 and 6 respectively.

Example 2
Preparation of Lactose (II)

Figure 7:
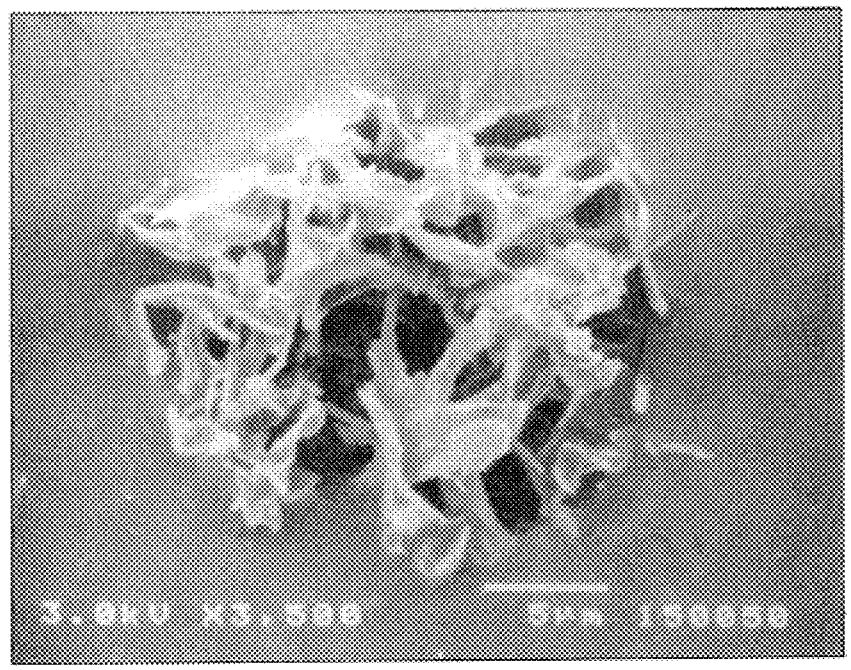
FIG. 7 is an SEM micrograph of lactose prepared according to Example 2.
Figure 8:
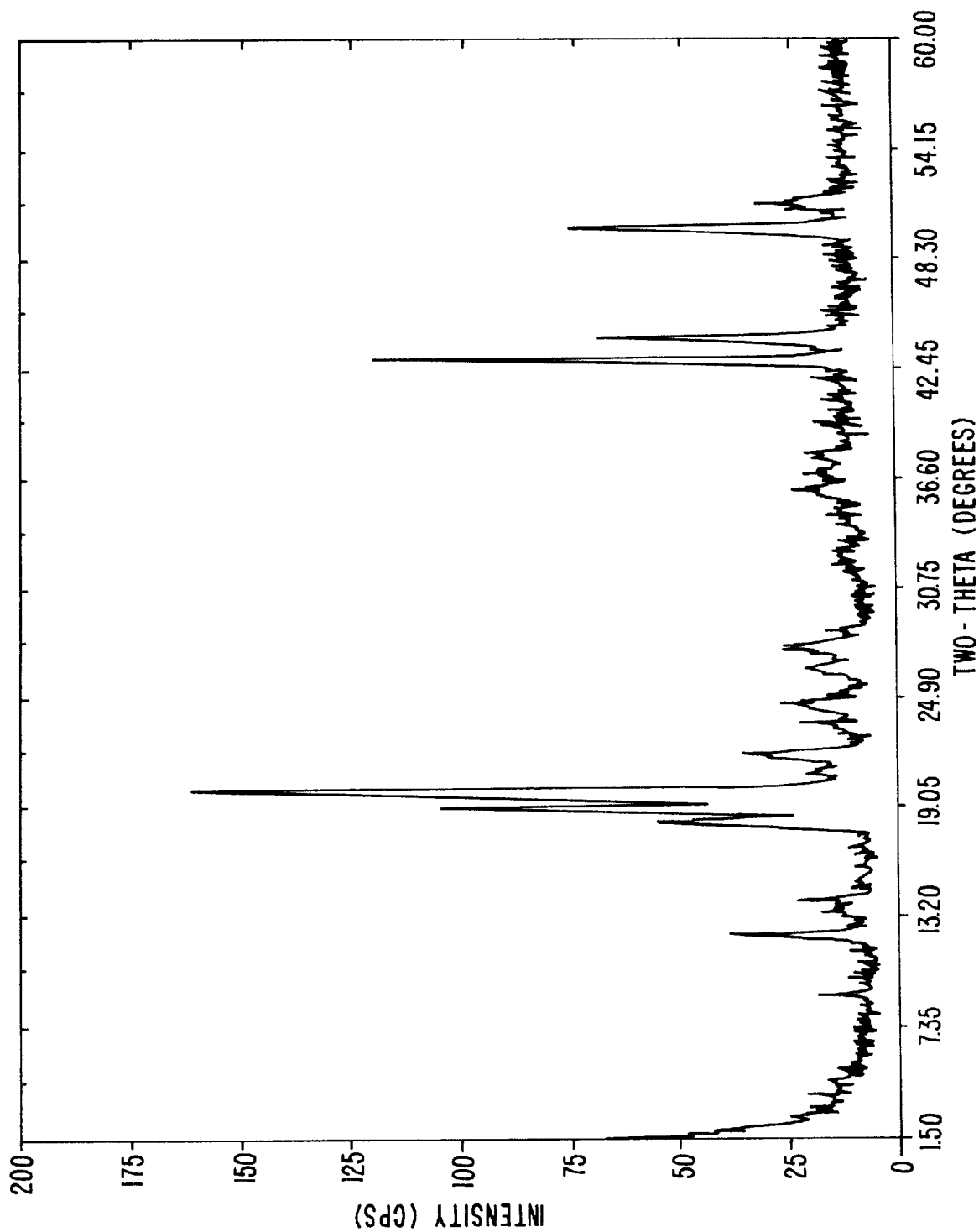
FIG. 8 is an XRD pattern for the sample shown in FIG. 7.

In an experiment similar to that of Example 1, a 0.5% w/v solution of alpha-lactose monohydrate in methanol:water (95:5 v/v) was prepared and delivered to a 50 ml high pressure particle formation vessel via a two-passage nozzle. The working conditions were 150 bar and 50° C. inside the vessel, with a flow rate of 0.7 ml/min for the solution and 9 ml/min for the supercritical $CO_2$. The collected product was a free flowing, fine white powder. FIGS. 7 and 8 show an SEM micrograph and XRD pattern respectively for this product.

The SEM micrographs for the products of Examples 1 and 2 reveal a marked difference in the shape of the lactose particles prepared under the different operating conditions. The XRD patterns indicate the crystalline nature of the products.

As can be seen from these examples, the present invention provides an extremely effective technique for the controlled formation of lactose particles using supercritical fluids, without loss of control over the size, shape, form and other properties of the resultant particles. This is achieved despite the fact that lactose has a very low solubility in many conventional organic solvents which would themselves be soluble in supercritical carbon dioxide, which has meant that previously it would not have been possible to precipitate lactose using supercritical carbon dioxide. Examples 3–5
Preparation of Other Sugars These examples illustrate the preparation of other sugars, which like lactose would be difficult to produce in particulate form using conventional methods.

The experiments were carried out using apparatus of the type shown in FIGS. 1 and 2, with the three-passage nozzle of FIG. 3. In accordance with the preferred version of the invention, a solution of the desired sugar in a first vehicle (water) was introduced into the nozzle separately from the second vehicle (ethanol), in which the sugar is substantially insoluble, but which is itself soluble in supercritical $CO_2$. The solution and the second vehicle came into contact only immediately prior to their dispersion by the supercritical fluid.

Note that in Examples 3 and 4, the product sugars had an amorphous nature, despite having been prepared from crystalline starting materials. Amorphous products have great advantages for use as carriers for pharmaceuticals, in that they have a relatively high surface area—they can therefore carry more of the pharmaceutical and can also dissolve more quickly than the equivalent crystalline forms. Their smooth surfaces facilitate the release of the carried pharmaceutical, making them ideal for delivery of drugs by, for instance, inhalation methods.

Using known particle formation methods, it is very difficult, and often very expensive, to produce such sugars in amorphous form. Examples 3–5 therefore highlight a highly advantageous application for the method of the present invention.

They also demonstrate the use of the invention to manipulate the shape and degree of crystallinity of particulate sugars. Such manipulation is difficult, if not impossible, to achieve using conventional crystallization methods.

Example 3
Preparation of Maltose 1.01 g of maltose monohydrate (Sigma UK) was dissolved in 5 ml of deionized water and introduced into a 32 ml particle formation vessel through the intermediate nozzle passage, at a flow rate of 0.03 ml/min. The vessel was maintained at 250 bar and 70° C. Absolute ethanol was co-introduced into the vessel through the inner nozzle passage, at a rate of 0.4 ml/min, and supercritical $CO_2$ through the outer passage at a rate of 9 ml/min. A free-flowing white powder was collected.

Figure 9:
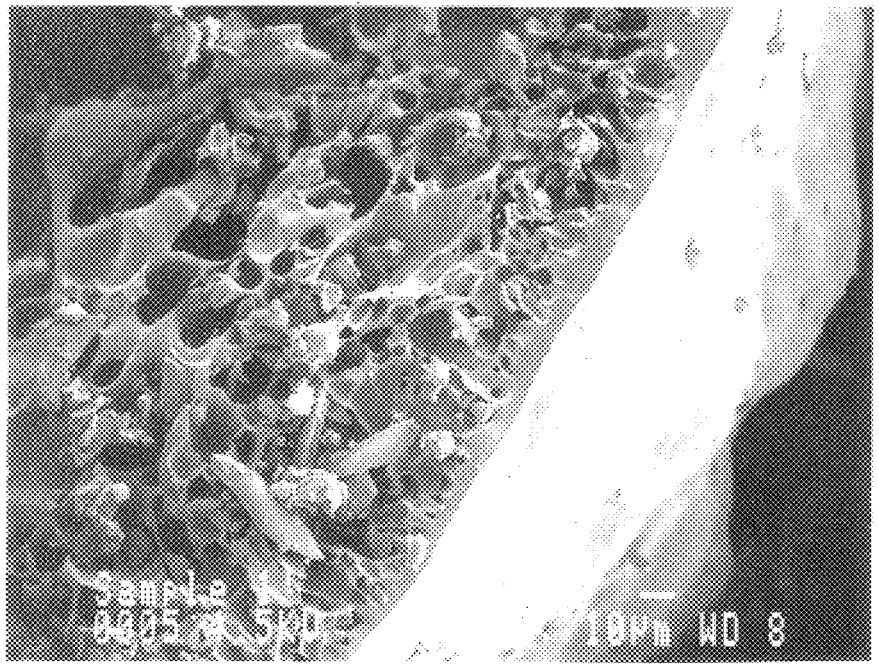
FIGS. 9 and 10 are SEM micrographs for the product and starting material (maltose) respectively of Example 3.
Figure 10:
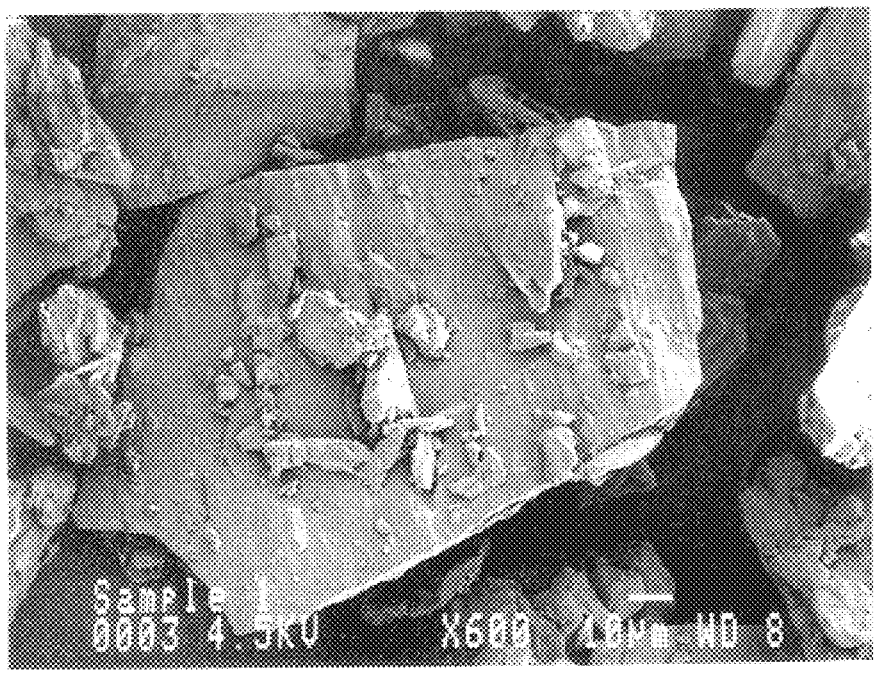
Figure 11:
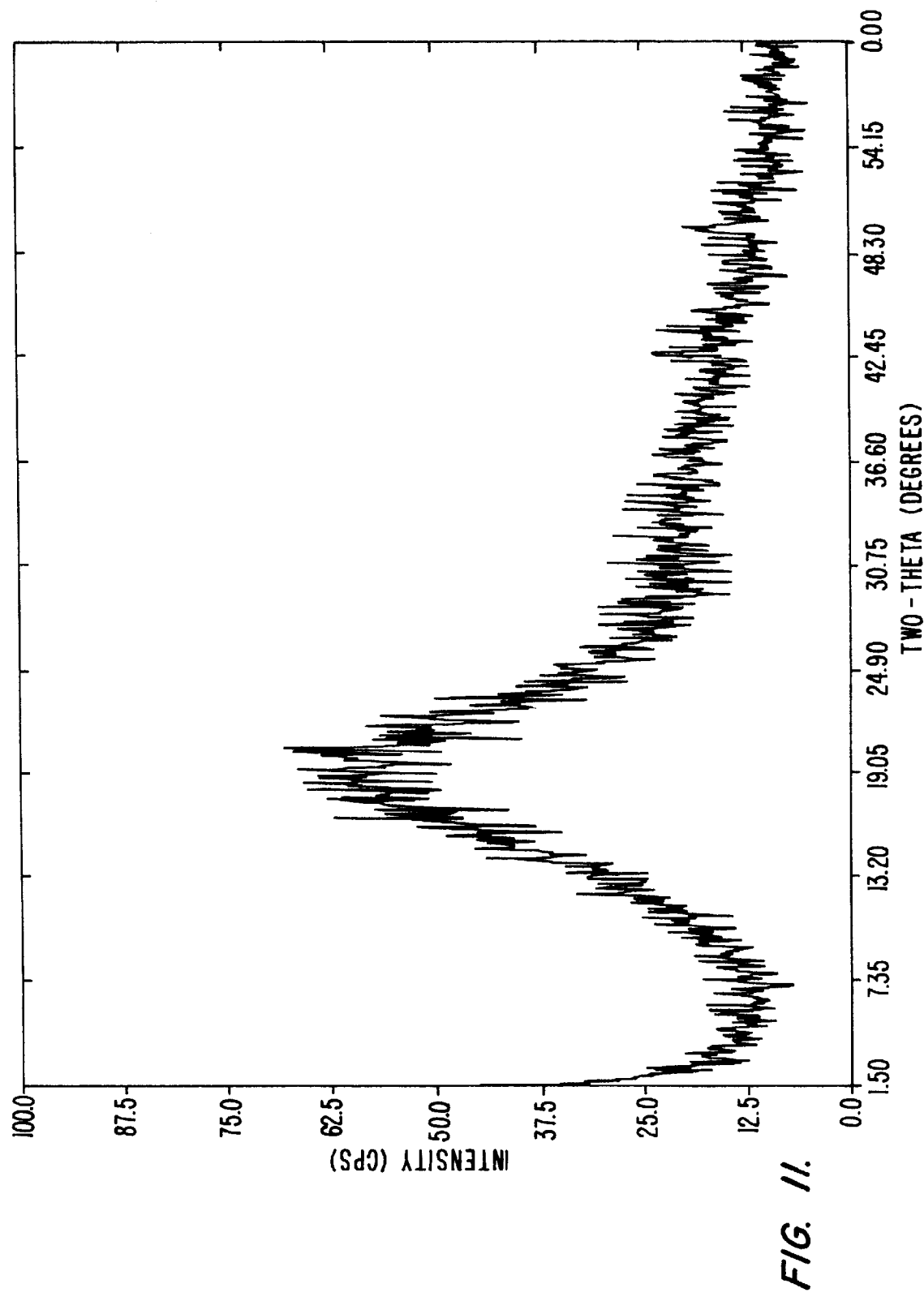
FIGS. 11 and 12 are XRD patterns for the samples shown in FIGS. 9 and 10 respectively.
Figure 12:
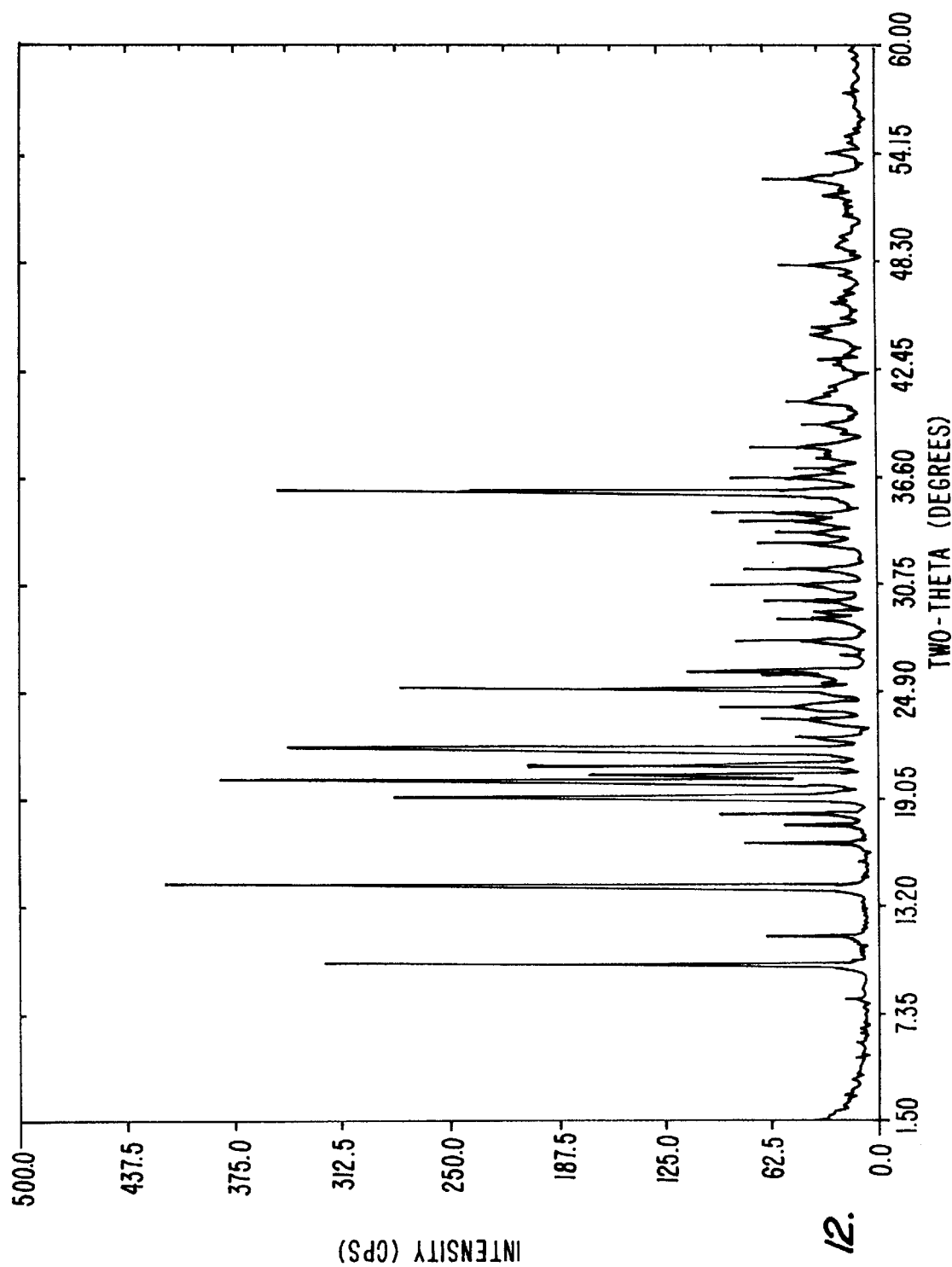

The SEM photographs for the product (FIG. 9) and. the starting material (FIG. 10) show a remarkable difference in crystal habit between the two solids. The product is in the form of spongy spheres with smooth surfaces; its XRD pattern (FIG. 11) reveals its amorphous nature compared with the crystalline nature of the maltose used as the starting material (see the XRD pattern in FIG. 12).

Example 4
Preparation of Trehalose

Trehalose is another sugar used as a carrier for pharmaceuticals and to protect proteins from unfolding under certain processing conditions. Its controlled preparation in particulate form is therefore highly desirable.

In this experiment, 1.01 g of alpha, alpha-trehalose dihydrate (Sigma UK) was dissolved in 4 ml of deionized water and introduced into a 32 ml particle formation vessel through the intermediate nozzle passage at a flow rate of 0.015 ml/min. The vessel was maintained at 250 bar and 70° C. Absolute ethanol was co-introduced into the vessel through the inner nozzle passage, at a rate of 0.4 ml/min, and supercritical CO, through the outer passage at a rate of 8 ml/min. A free-flowing white powder was collected.

Figure 13:
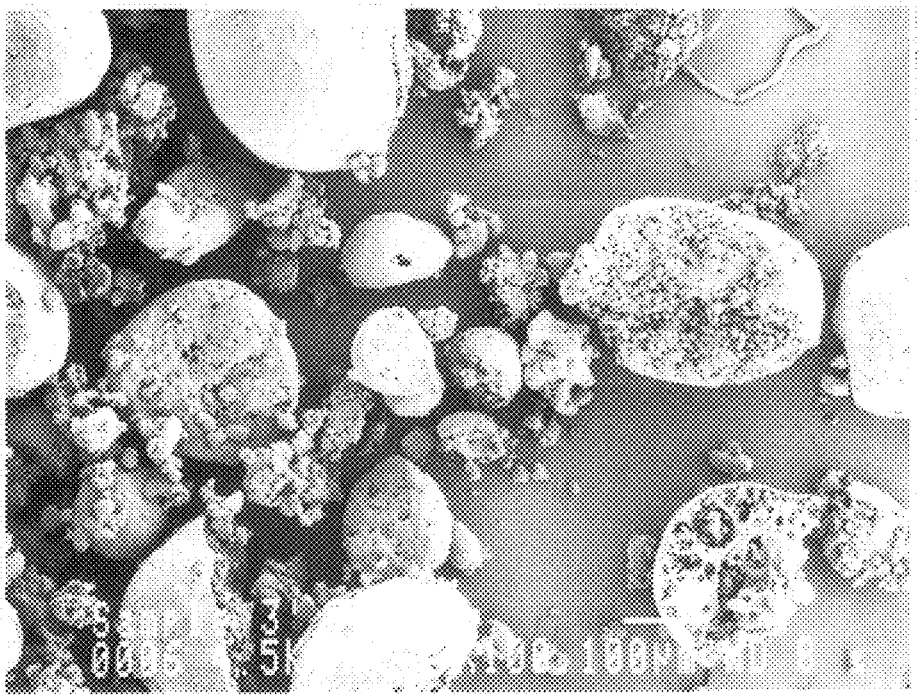
FIGS. 13 and 14 are SEM micrographs for the product and starting material (trehalose) respectively of Example 4.
Figure 14:
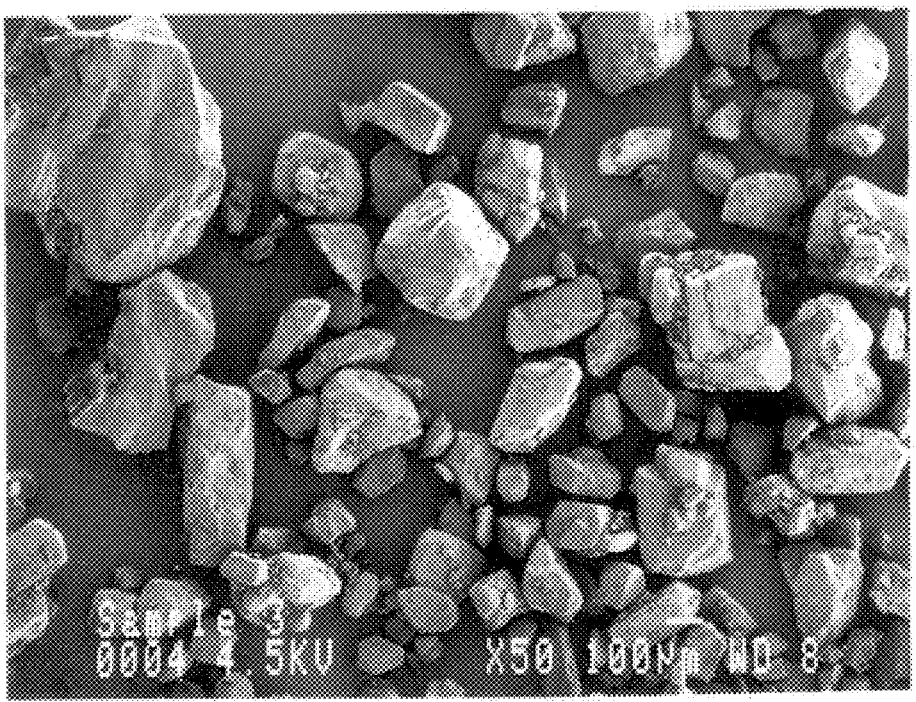
Figure 15:
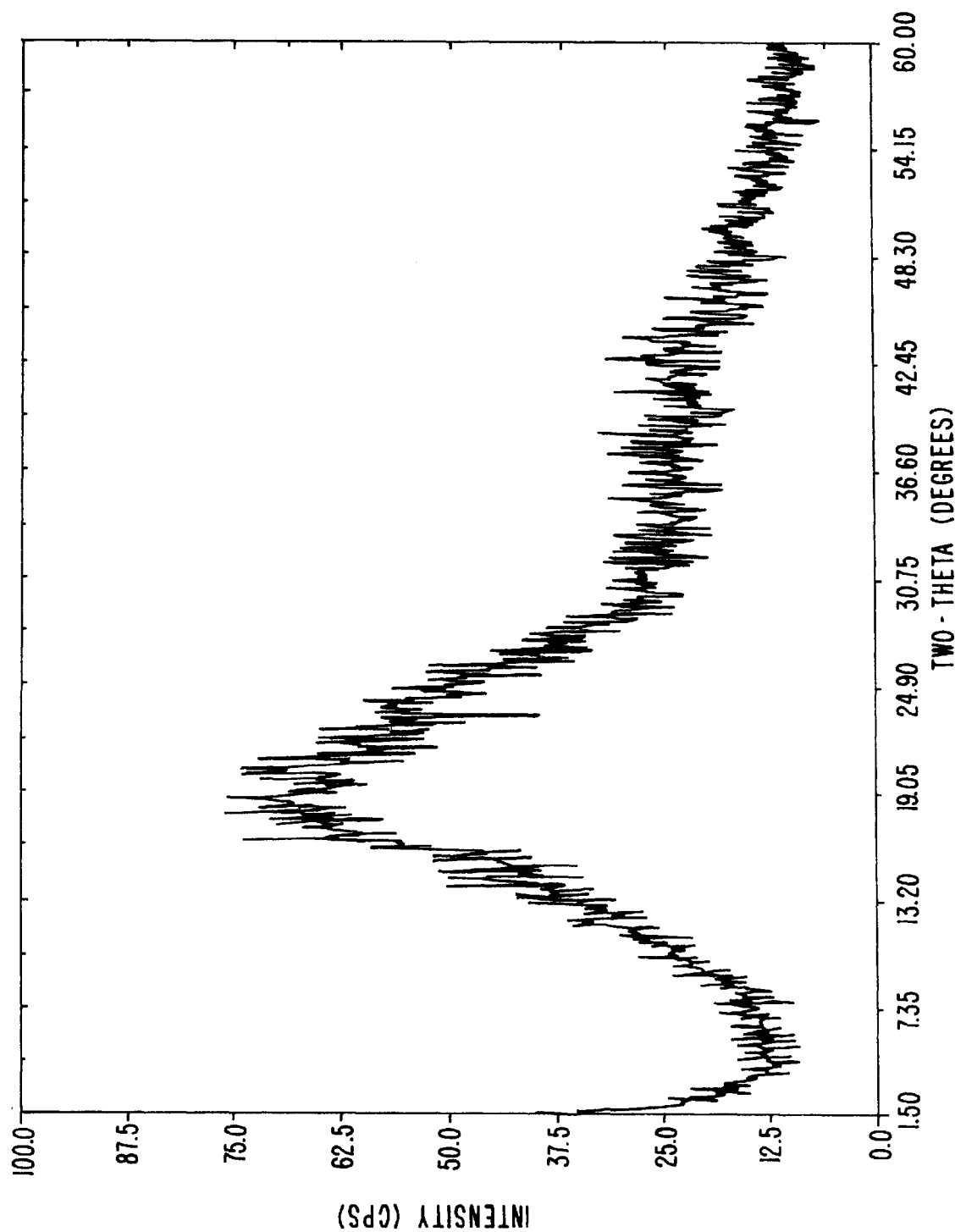
FIGS. 15 and 16 are XRD patterns for the samples shown in FIGS. 13 and 14 respectively.
Figure 16:
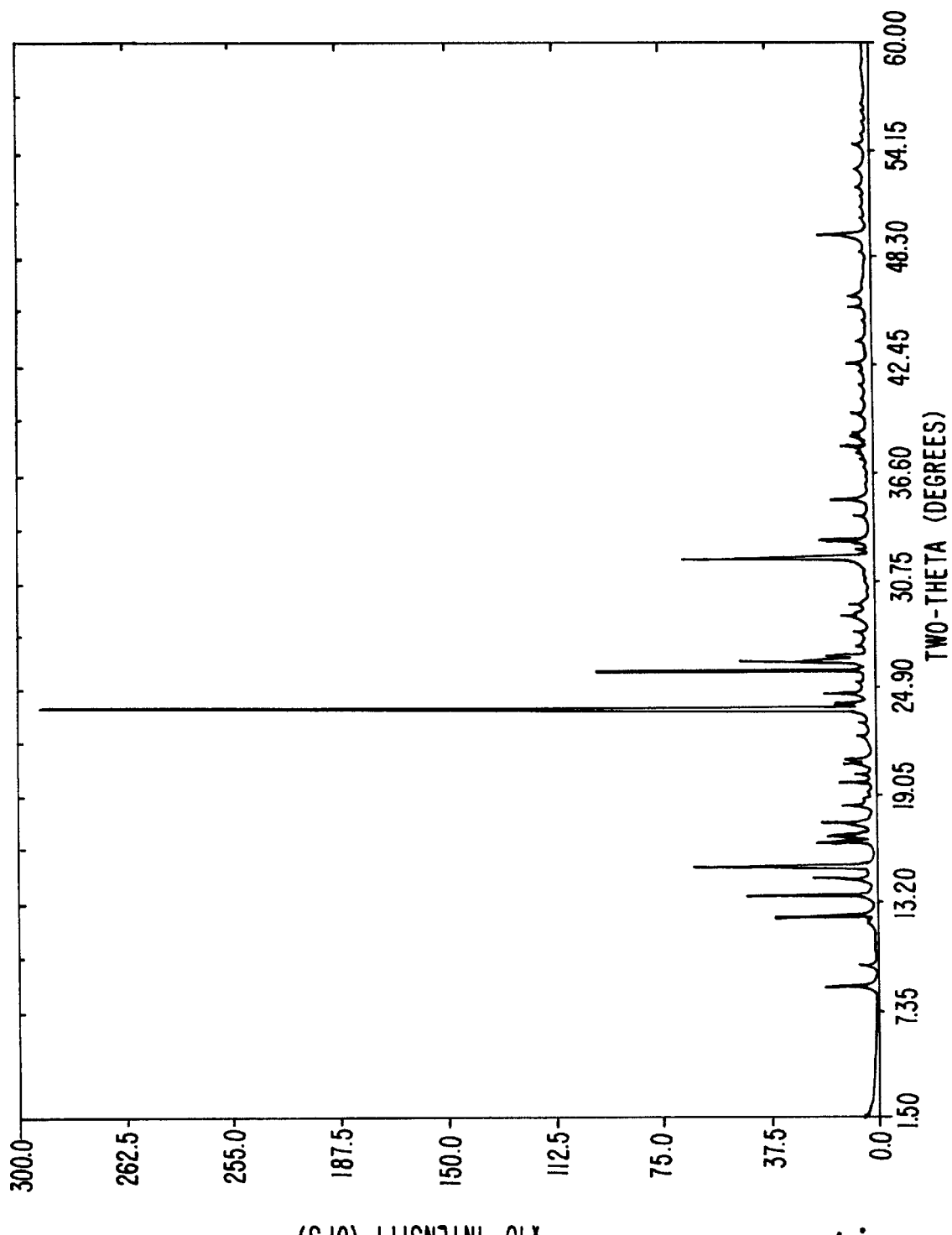

The SEM micrographs for the product (FIG. 13) and the starting material (FIG. 14) again show a considerable difference in crystal habit between the two solids. The product is in the form of spongy, smooth-surfaced particles with an enhanced surface area. The XRD pattern for the product (FIG. 15) reveals its amorphous nature compared with the crystalline starting material (FIG. 16).

Example 5
Preparation of Sucrose 2.04 g of sucrose (Sigma UK) was dissolved in 10 ml of deionized water and introduced into a 32 ml particle formation vessel through the intermediate nozzle passage, at a flow rate of 0.02 ml/min. The vessel was maintained at 250 bar and 60° C. Absolute ethanol was co-introduced into the vessel through the inner nozzle passage, at a rate of 0.35 ml/min, and supercritical $CO_2$ through the outer passage at a rate of 8 ml/min. A free-flowing white powder was collected.

Figure 17:
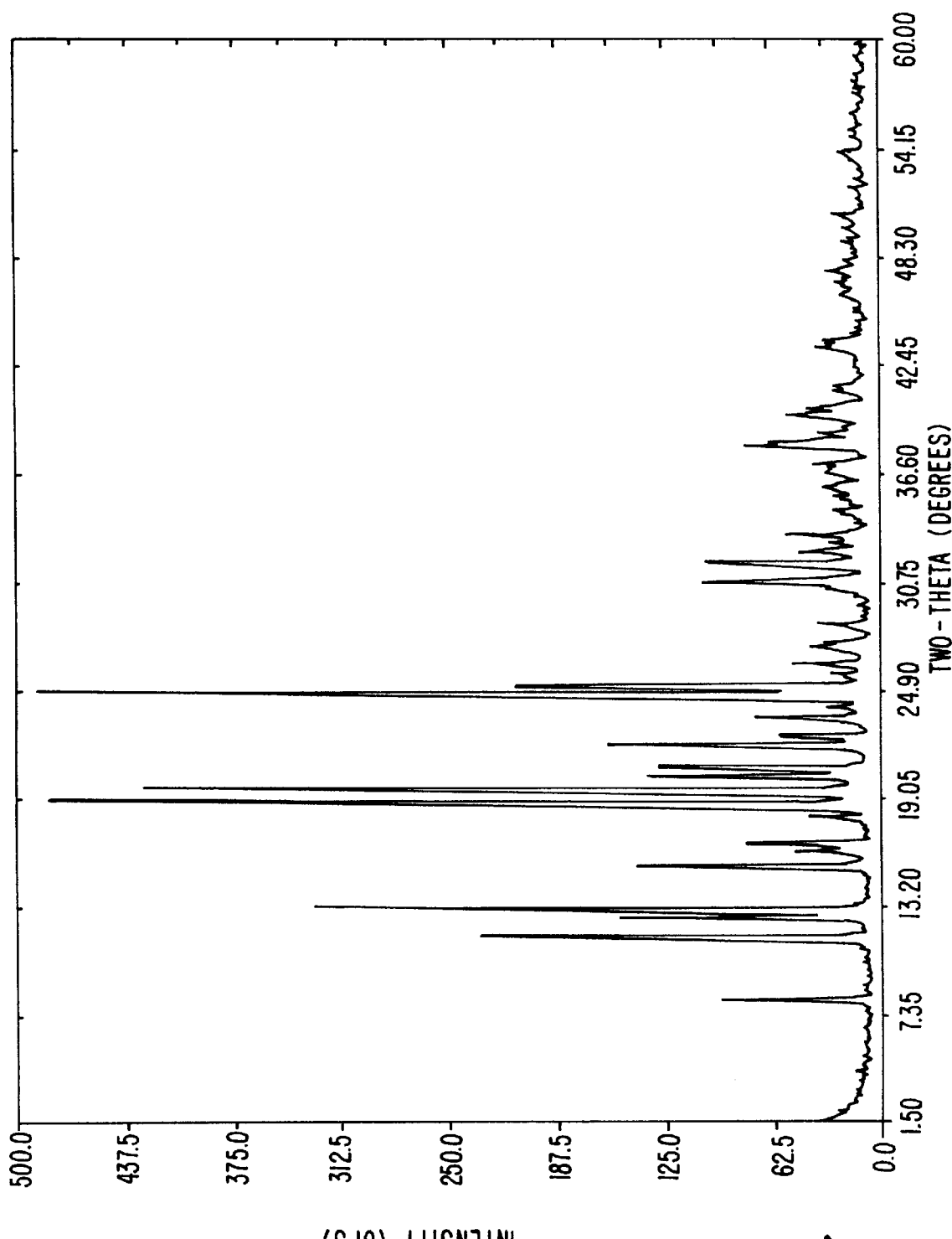
FIG. 17 is an XRD pattern for sucrose prepared according to Example 5.

The XRD pattern for the product (FIG. 17) reveals a crystalline nature.

Example 6

Figure 18:
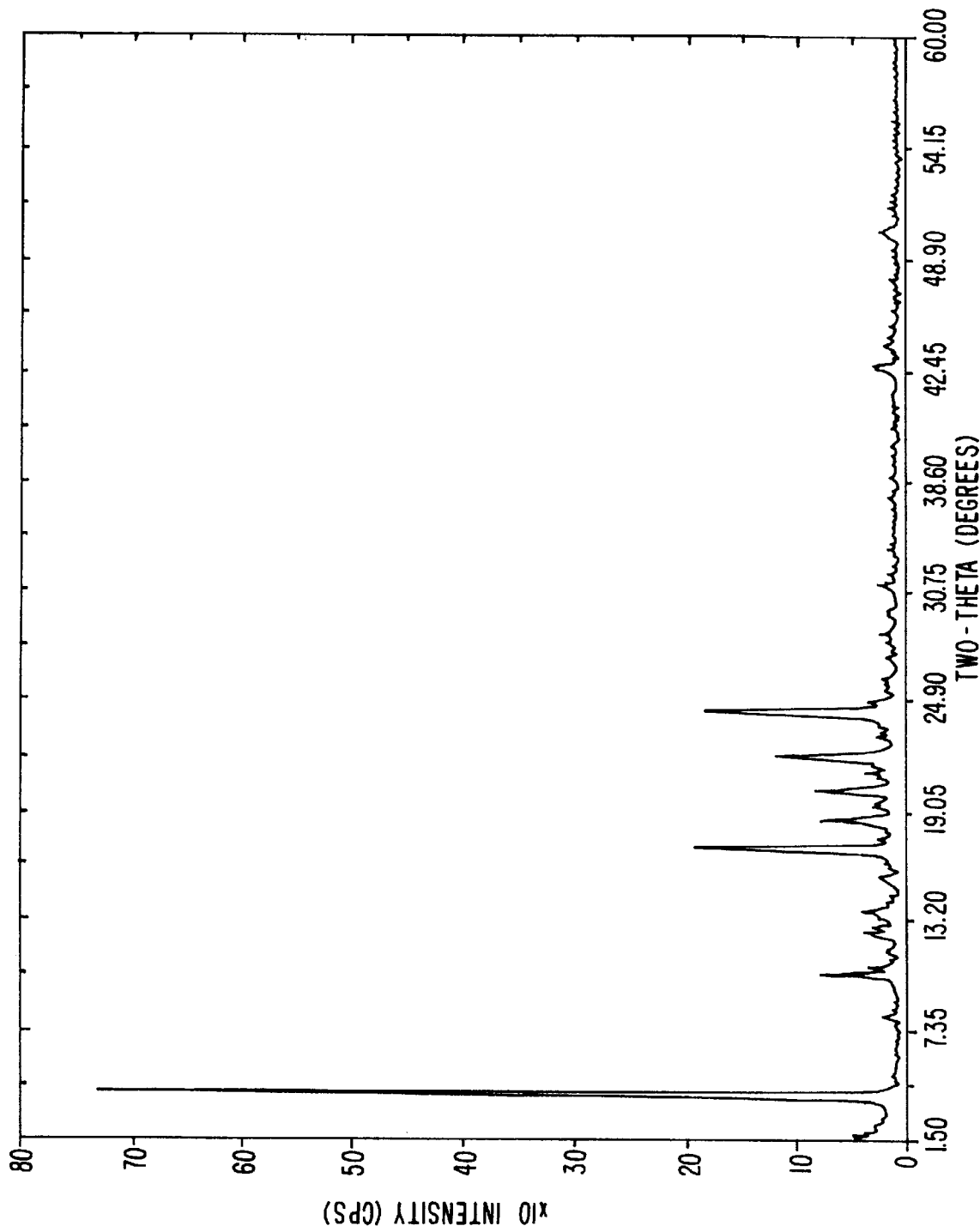
FIG. 18 is an XRD pattern for salmeterol xinafoate prepared according to Example 6.

1% w/v solution of salmeterol xinafoate in acetone was mixed at a rate of 0.1 ml/min with 0.4 ml/min of n-hexane (antisolvent) prior to introduction to the particle formation vessel through the intermediate passage of the three-component nozzle as in FIG. 4A. Supercritical $CO_2$ was fed at a rate of 15 ml/min through the inner and outer passages to disperse the magma (acetone solution, hexane and the continuously growing salmeterol nuclei/embryos) and extract the acetone-hexane solvent mixture. The particle formation vessel was maintained at 150 bar and 60° C. A fine, free-flowing powder product was collected and examined by XRD. FIG. 18 shows the XRD pattern which indicates a crystalline polymorph I of the drug material.

This result demonstrates the effectiveness of these methods and apparatus to influence crystallization by addition of antisolvents before dispersion by the supercritical fluid. The opportunity is provided to control nucleation and growth of particles by controlling the relative rate of addition of the solution of the material of interest to the antisolvent, or vice versa.

Example 7
Preparation of Protein Particles

In this example, the method of the invention was used to prepare the water-soluble protein R-TEM beta-lactamase, again using two vehicles. An aqueous protein solution was co-introduced into a particle formation vessel of the type shown in FIGS. 1 and 2 with a second vehicle, ethanol, which is both miscible with water and soluble in supercritical $CO_2$. The two fluids were introduced, with the supercritical $CO_2$, through a three-passage nozzle of the type shown in FIG. 3, in such a way that contact between the aqueous solution and the ethanol, dispersion of the solution and the ethanol and extraction of the water and the ethanol all occurred very close together in time. It is thought that the aqueous solution and the ethanol "mixed" on contact, and that the water and ethanol were extracted together into the supercritical $CO_2$, despite the insolubility of water in the supercritical fluid.

A 0.25% w/v solution of R-TEM beta-lactamase (kindly provided by the Center for Applied Microbiology, Porton Down, Salisbury SP4 0JG, batch number 1TEM1L88) in deionized water was fed to the 32 ml particle formation vessel via the inner passage of the three-passage nozzle, at a flow rate of 0.04 ml/min. Absolute ethanol was co-introduced through the intermediate nozzle passage at a rate of 0.4 ml/min and supercritical $CO_2$ through the outer passage at a rate of 8 ml/min.

Here, the method of the invention, and the use of a three-passage nozzle allowed the aqueous protein solution to be mixed with the ethanol immediately prior to dispersion of the two vehicles by the supercritical fluid. The contact time between the aqueous and the organic fluids was so short that the risk of protein unfolding or denaturing was minimal—another advantage of using the present invention to prepare proteins and other active products.

The particulate product formed retained substantial enzymatic activity when tested calorimetrically using the chromogenic cephalosporin Nitrocefin (Oxoid, Unipath Limited, Basingstoke, Hampshire, England) and the assay method of O'Callaghan (C. H. O'Callaghan, A. Morris, S. Kirby and A. H. Shingler, *Antimicrobial Agents and Chemotherapy*, 1, pp283–288 (1972)). This illustrates the successful use of the method and apparatus of the invention in preparing particulate protein products in a controlled manner, even where the proteins are insoluble in, or incompatible with, organic solvents.

The above examples show how the apparatus and method of the present invention can be used to produce particulate products of various types in a highly controlled manner, without the usual solvent constraints. Applications of the invention might include for instance:

producing controlled size and shape particles of products for use in the pharmaceutical, photographic, ceramics, explosives/propellants, dyestuffs and food industries and others, especially of products which decompose or are otherwise compromised when subjected to conventional particle formation and milling techniques.

producing solid, stable forms of molecules and macromolecules which are difficult to process or freeze dry (e.g. proteins, peptides and polymers generally).

producing a particular polymorphic form of a compound or separating and/or enriching mixtures of isomers (including optical isomers) or polymorphs.

purifying drugs and other products, by removal of trace impurities (including solvents) using controlled selective precipitation (eg. using the invention to precipitate the impurities themselves).

coating substrates in a controlled manner, including with thin film liquid coatings.

controlling "doping" of compounds in products based on crystal lattices, or producing intimate blends-of two or more products, such as one product within a matrix of another, or one product coated onto or coated with another.

preparing completely new phases or materials under conditions not achievable using conventional particle formation techniques.

We claim:

1. A method for forming a particulate product, the method comprising (a) co-introducing into a particle formation vessel, the temperature and pressure in which are controlled, a supercritical fluid; a solution or suspension of a substance in a first vehicle; and, separately from the solution or suspension, a second vehicle which is substantially soluble in the supercritical fluid; and (b) using the supercritical fluid to disperse the solution or suspension and the second vehicle, and to extract the vehicles, substantially simultaneously and substantially immediately on introduction of the fluids into the particle formation vessel, wherein the first and second vehicles may mix to allow their extraction together into the supercritical fluid, and wherein contact between the solution or suspension and the second vehicle occurs either substantially simultaneously with, or immediately before, dispersion of the solution or suspension and the second vehicle by the action of the supercritical fluid and extraction of the vehicles by the supercritical fluid.

2. A method according to claim 1, wherein a flow rate of the second vehicle into the particle formation vessel to greater than that of the solution or suspension.

3. A method according to claim 1, wherein the amount of the first vehicle used is less than or equal to about 30% of the total amount of the first and second vehicles used.

4. A method according to claim 1, wherein the supercritical fluid contains one or more modifiers.

5. A method according to claim 1, wherein one of the two vehicles contains functional groups that may interact, through hydrogen-bonding or dipole-dipole interactions, with functional groups contained in the other vehicle.

6. A method according to claim 1, wherein the substance and the first vehicle are substantially polar and the second vehicle is substantially non-polar.

7. A method according to claim 1, wherein the substance and the first vehicle are substantially non-polar and the second vehicle is substantially polar.

8. A method according to claim 1 wherein the substance is substantially insoluble in the second vehicle.

9. A method in accordance to claim 8, wherein the second vehicle contains a crystallization seed of a material which is insoluble in the second vehicle to induce nucleation of the substance when the second vehicle comes into contact with the solution or suspension of the substance in the first vehicle.

10. A method in accordance to claim 9, wherein the substance is a pharmaceutical substance, and the seed comprises a pharmaceutically acceptable carrier for the substance.

11. A method according to claim 1, wherein the supercritical fluid, the solution or suspension and the second vehicle are co-introduced into the particle formation vessel by means of a nozzle having an outlet end communicating with the interior of the particle formation vessel, and two or more-coaxial passages which terminate adjacent or substantially adjacent to one another at the outlet end, at least one of the passages serving to introduce a flow of the supercritical fluid into the particle formation vessel, at least one of the passages serving to introduce a flow of the solution or suspension of the substance in the first vehicle and at least one of the passages serving to introduce a flow of the second vehicle.

12. A method according to claim 11, wherein the solution or suspension of the substance in the first vehicle is introduced into the particle formation vessel through one passage of the nozzle, and the supercritical fluid and the second vehicle are introduced together through another passage of the nozzle, and mixing of the two vehicles occurs substantially simultaneously with their dispersion and extraction by the supercritical fluid.

13. A method according to claim 12, wherein the nozzle has at least three coaxial passages, the solution or suspension being introduced between an inner and an outer flow of the supercritical fluid/second vehicle mixture.

14. A method according to claim 11, wherein the nozzle has at least three coaxial passages, the outlet of at least one of the inner nozzle passages being located a small distance upstream of the outlet of one of its surrounding passages, the distance being sufficient to allow a degree of pre-mixing to occur between fluids introduced through said inner and surrounding passages, and wherein the solution or suspension and the second vehicle are introduced through the inner passage and surrounding passage in question so as to allow, in use, a degree of mixing to occur, between the solution or suspension and the second vehicle, within the nozzle.

15. A method according to claim 14, wherein the nozzle has at least four coaxial passages, and wherein the solution or suspension and the second vehicle are introduced into the particle formation vessel between an inner and an outer flow of the supercritical fluid.

16. A method according to claim 1, wherein one or more of the following conditions is varied in order to control the size and/or size distribution and/or shape and/or crystalline form of the particulate product formed: the flow rate(s) of the supercritical fluid and/or the solution or suspension and/or the second vehicle; the relative amounts of the two vehicles; the concentration of the substance in the first vehicle; the temperature inside the particle formation vessel; and the pressure inside the particle formation vessel.

17. A method according to claim 1, wherein the ratio of the solution/suspension flow rate, into the particle formation vessel, to that of the supercritical fluid is between 0.001 and 0.2.

18. A method according to claim 1, which is carried out in a plural batch manner by switching between two or more particle formation vessels or between two or more means for collecting the particulate product.

19. Apparatus for use in carrying out a method according to claim 1, the apparatus comprising a particle formation vessel; means for controlling the temperature in the vessel at a desired level; means for controlling the pressure in the vessel at a desired level; and means for the co-introduction, into the vessel, of the supercritical fluid, the solution or suspension of the substance in the first vehicle, and the second vehicle, in such zL way that contact between the solution or suspension and the second vehicle occurs either substantially simultaneously with, or immediately before, dispersion of the solution or suspension and the second vehicle by the action of the supercritical fluid and extraction of the vehicles by the supercritical fluid, and such that the dispersion and extraction occur substantially simultaneously and substantially immediately on introduction of the fluids onto the particle formation vessel, wherein the means for the co-introduction of the fluids into the vessel comprises a nozzle having an outlet end communicating with the interior of the vessel, and at least three coaxial passages which terminate adjacent or substantially adjacent to one another at the outlet end, at least one of the passages serving to introduce a flow of the supercritical fluid into the vessel, at least one of the passages serving to introduce a flow of the solution or suspension and at least one of the passages serving to introduce a flow of the second vehicle, all fluid flows being in substantially coaxial directions, and wherein the outlet of at least one of the inner nozzle passages is located a small distance upstream of the outlet of one of its surrounding passages, the distance being sufficient to allow a degree of mixing to occur within the nozzle between the solution or suspension and the second vehicle when the solution/suspension and the second vehicle are introduced through the inner passage and surrounding passage in question.

20. Apparatus according to claim 19, wherein the nozzle has four coaxial passages.

21. Apparatus according to claim 19, wherein the angle of taper of the outlet end of the nozzle, with respect to the main axis of the nozzle, is in the range of about 10° to about 60°.

22. Apparatus according to claim 19, comprising more than one particle formation vessel and/or more than one means for collecting the particulate product, thereby allowing for the apparatus to be used in a plural batch manner by switching from one particle formation vessel or collection means to another as required.

* * * * *